US009173894B2

(12) United States Patent
Dean et al.

(10) Patent No.: US 9,173,894 B2
(45) Date of Patent: *Nov. 3, 2015

(54) METHOD OF TREATING KELOIDS OR HYPERTROPHIC SCARS USING ANTISENSE COMPOUNDS TARGETING CONNECTIVE TISSUE GROWTH FACTOR (CTGF)

(75) Inventors: Nicholas M. Dean, Encinitas, CA (US); Lincoln Krochmal, Los Gatos, CA (US); Gregory Hardee, Del Mar, CA (US); J. Gordon Foulkes, Encinitas, CA (US); Niall O'Donnell, Encinitas, CA (US); Leroy Young, Wildwood, MO (US); Mark Jewell, Eugene, OR (US)

(73) Assignee: Excaliard Pharamaceuticals, Inc., New York, NY (US)

( * ) Notice: Subject to any disclaimer, the term of this patent is extended or adjusted under 35 U.S.C. 154(b) by 369 days.

This patent is subject to a terminal disclaimer.

(21) Appl. No.: 13/364,547

(22) Filed: Feb. 2, 2012

(65) Prior Publication Data

US 2012/0238937 A1    Sep. 20, 2012

Related U.S. Application Data

(60) Provisional application No. 61/438,879, filed on Feb. 2, 2011, provisional application No. 61/488,666, filed on May 20, 2011, provisional application No. 61/527,821, filed on Aug. 26, 2011.

(51) Int. Cl.
| | | |
|---|---|---|
| *A61K 48/00* | (2006.01) | |
| *A61K 31/7088* | (2006.01) | |
| *A61K 31/712* | (2006.01) | |
| *A61K 45/06* | (2006.01) | |

(52) U.S. Cl.
CPC ........... *A61K 31/7088* (2013.01); *A61K 31/712* (2013.01); *A61K 45/06* (2013.01)

(58) Field of Classification Search
None
See application file for complete search history.

(56) References Cited

U.S. PATENT DOCUMENTS

| | | |
|---|---|---|
| 5,585,270 A | 12/1996 | Grotendorst et al. |
| 5,783,187 A | 7/1998 | Grotendorst et al. |
| 5,801,154 A | 9/1998 | Baracchini et al. |
| 5,876,730 A | 3/1999 | Brigstock et al. |
| 5,998,148 A | 12/1999 | Bennett et al. |
| 6,069,006 A | 5/2000 | Grotendorst et al. |
| 6,150,101 A | 11/2000 | Grotendorst et al. |
| 6,232,064 B1 | 5/2001 | Grotendorst et al. |
| 6,358,741 B1 | 3/2002 | Schmidt et al. |
| 6,436,909 B1 | 8/2002 | Dean et al. |
| 6,965,025 B2 | 11/2005 | Gaarde et al. |
| 7,399,845 B2 | 7/2008 | Seth et al. |
| 7,666,853 B2 | 2/2010 | Khvorova et al. |
| 7,709,630 B2 | 5/2010 | Gaarde et al. |
| 7,718,177 B2 | 5/2010 | Grotendorst et al. |
| 7,820,809 B2 | 10/2010 | Khvorova et al. |
| 7,833,989 B2 | 11/2010 | Khvorova et al. |
| 2003/0119010 A1 | 6/2003 | Powell et al. |
| 2003/0153524 A1 | 8/2003 | Hinton et al. |
| 2003/0180300 A1 | 9/2003 | Grotendorst |
| 2003/0180891 A1 | 9/2003 | Young et al. |
| 2004/0259247 A1 | 12/2004 | Tuschl et al. |
| 2005/0059629 A1 | 3/2005 | Gaarde et al. |
| 2005/0136502 A1 | 6/2005 | Riser et al. |
| 2007/0299028 A1 | 12/2007 | Siwkowski et al. |
| 2008/0015114 A1 | 1/2008 | Khvorova et al. |
| 2008/0050329 A1 | 2/2008 | De La Poterie |
| 2008/0070856 A1 | 3/2008 | Kreutzer et al. |
| 2008/0119433 A1 | 5/2008 | Tabor |
| 2008/0125352 A1 | 5/2008 | Brigstock et al. |
| 2008/0193443 A1 | 8/2008 | Beskrovnaya et al. |
| 2008/0206256 A1 | 8/2008 | Spong et al. |
| 2009/0069623 A1 | 3/2009 | Oh |
| 2009/0156524 A1 | 6/2009 | Feinstein et al. |
| 2009/0162365 A1 | 6/2009 | Feinstein et al. |
| 2010/0130595 A1 | 5/2010 | Dean et al. |
| 2010/0266532 A1 | 10/2010 | Ferguson |
| 2011/0112168 A1 | 5/2011 | Feinstein et al. |

FOREIGN PATENT DOCUMENTS

| | | |
|---|---|---|
| AU | 2009275387 | 8/2009 |
| EP | 1461352 | 7/2006 |
| EP | 2388318 | 11/2011 |
| GB | 2465902 | 12/2010 |
| WO | 96/38172 | 12/1996 |
| WO | 99/66959 | 12/1999 |
| WO | 00/13706 | 3/2000 |
| WO | 00/27868 | 5/2000 |
| WO | 00/35936 | 6/2000 |
| WO | 00/35939 | 6/2000 |
| WO | 01/29217 | 4/2001 |
| WO | 03/053340 | 7/2003 |
| WO | 01/85941 | 11/2003 |
| WO | 2005/050202 | 6/2005 |
| WO | 2005/050203 | 6/2005 |

(Continued)

OTHER PUBLICATIONS

Abreu et al., "Connective tissue growth factor {CTGF} modulates cell signalling by BMP and TGF-beta", Nat Cell Biol., 4(8):599-604 (2002).
Adler et al., "Glomerular mRNAs in Human Type 1 Diabetes: Biochemical Evidence for Microalbuminuria as a Manifestation of Diabetic Nephropathy," Kidney International, 2330-2336, (2001).
Advisory Action issued Feb. 17, 2005 in connection with U.S. Appl. No. 10/006,191.
Agrawal et al., "Antisense Therapeutics: Is It As Simple As Complementary Base Recognition?," Molecular Med. Today, 6:72-81, (2000).
Allawi et al., "Mapping of RNA accessible sites by extension of random oligonucleotide libraries with reverse transcriptase," RNA, 7:314-327, (2001).

(Continued)

*Primary Examiner* — Kimberly Chong
(74) *Attorney, Agent, or Firm* — Raquel M. Alvarez

(57) ABSTRACT

This invention provides methods of preventing formation of, or treating, fibrotic lesions, including skin scars such as keloids and hypertrophic scars which comprise administering to the subject by one or more injection a compound which comprises a modified oligonucleotide, such as a modified antisense oligonucleotide, siRNA, or oligodeoxyribonucleotide, which inhibits expression of protein involved in fibrosis. Dosing of the antisense using an intradermal threading technique is also described.

27 Claims, 9 Drawing Sheets

(56) References Cited

FOREIGN PATENT DOCUMENTS

| | | |
|---|---|---|
| WO | 2005/077413 | 8/2005 |
| WO | 2005/110479 | 11/2005 |
| WO | 2005/117941 | 12/2005 |
| WO | 2005/120231 | 12/2005 |
| WO | 2006/069037 | 6/2006 |
| WO | 2006/122046 | 11/2006 |
| WO | 2007/040636 | 4/2007 |
| WO | 2009/044392 | 4/2009 |
| WO | 2010/027830 | 3/2010 |
| WO | 2010/027831 | 3/2010 |
| WO | 2010/033246 | 3/2010 |
| WO | 2010/036111 | 4/2010 |
| WO | 2010/042201 | 4/2010 |
| WO | 2010/042202 | 4/2010 |
| WO | 2010/042281 | 4/2010 |
| WO | 2010/107952 | 9/2010 |
| WO | 2011/002525 | 1/2011 |

OTHER PUBLICATIONS

Allen, J.T. et al., "Enhanced insulin-like growth factor binding protein-related protein 2 (Connective tissue growth factor) expression in patients with idiopathic pulmonary fibrosis and pulmonary sarcoidosis," Am. J. Respir. Cell Mol. Biol. 21(6) :693-700, (1999).
Amendment in Response to Mar. 31, 2011 Office Action file Sep. 30, 2011 in connection with U.S. Appl. No. 12/547,481.
Babic et al., "Fispl2/mouse connective tissue growth factor mediates endothelial cell adhesion and migration through integrin alphavbeta3, promotes endothelial cell survival and induces angiogenesis in vivo," Mol. Cell Biol. 19:2958-2966, (1999).
Blalock et al., "Connective tissue growth factor expression and action in human corneal fibroblast cultures and rat corneas after photorefractive keratectomy," Invest Ophthalmol Vis Sci., 44(5):1879-87, (2003).
Boes et al., "Connective tissue growth factor (IGFBP-rP2) expression and regulation in cultured bovine endothelial cells," Endocrinology, 140:1575-1580, (1999).
Bonniaud, et al., "Adenoviral gene transfer of connective tissue growth factor in the lung induces transient fibrosis," Am J Respir Crit Care Med., 68(7) :770-8, (2003).
Bradham, D.M. et al., "Connective tissue growth factor: a cysteine-rich mitogen secreted by human vascular endothelial cells is related to the SRC-induced immediate early gene product CEF-10," J. Cell Biol., 114:1285-1294, (1991).
Chirilla et al. "The Use of Synthetic Polymer for 62. Delivery of Therapeutic Antisense Oligodeoxynucleotides," Biomaterials, 23:321-342, (2002).
Colwell A.S,, et al., "Fetal and adult fibroblasts have similar dependent signaling pathways," 117(7):2277-83 TGF-beta-mediated, Plast Reconstr SmadSurg, (2006).
Combined Search and Examination Report issued Jun. 22, 2010 in connection with British Patent Application No. GB1002626.8.
Crooke, "Progress in Antisense Technology," Ann. Rev. Medicine, 55:61-95, (2004).
Dammeier J., et al., "Is a novel potent inducer of connective tissue growth factor expression. Implications for glucocorticoid therapy," J Biol Chem 273(29) :18185-90 (1998).
Dun, et al., Accession No. AZ781130 on database rst.seq, Feb. 16, 2001.
Duncan, M.R. et al., "Connective tissue growth factor mediates transforming growth factor f-induced collagen synthesis: down-regulation by cAMP," Faseb J., 13:1774-1786, (1999).
Examination Report issued Jun. 8, 2011 in connection with New Zealand Patent Application No. 591416.
Examiner Interview Summary issued Sep. 11, 2009 in connection with U.S. Appl. No. 11/985,843.
Frazier, K. et al., "Stimulation of fibroblast cell growth, matrix production, and granulation tissue formation by connective tissue growth factor," J Invest Dermatol., 107(3) :404-11, (1996).

Grotendorst, et al., "Combinatorial signaling pathways determine fibroblast proliferation and myofibroblast differentiation," Faseb J., 18{3):469-79, (2004).
Grotendorst, G. R., "Connective tissue growth factor: a mediator of TGF-beta action on fibroblasts," Cytokine Growth Factor Rev., 8(3):171-9 (1997).
Hillier et al., Accession No. R06912 on database rst. seq, Apr. 5, 1995.
Hishikawa, K., et al,. "Connective Tissue Growth Factor Induces Apoptosis in Human Breast Cancer Cell Line MCF-7," J. Biol. Chem., 274:37461-37466, (1999).
Hishikawa, K. et al., "Transforming growth factor-IH induces apoptosis via connective tissue growth factor in human aortic smooth muscle cells," Eur. J. Pharmacal., 385:287-290, (1999).
Hishikawa, K. et al., "Static Pressure Regulates Connective Tissue Growth Factor Expression in Human Mesangial Cells," J. Biol. Chem., 276:16797-16803, (2001).
Ho et al., "Mapping of RNA accessible sites for antisense experiments with oligonucleotide libraries," Nature Biotech. 16:59-63, (1998).
Igarashi A., et al., "Connective tissue growth factor gene expression in tissue sections from localized scleroderma, keloid, and other fibrotic skin disorders," The Journal of investigative dermatology 106(4):729-33, (1996).
Igarashi A., et al., "Regulation of connective tissue growth factor gene expression in human skin fibroblasts and during wound repair," Mol Biol Cell., 4 {6) :637-45, (1993).
Ito, Y. et al., "Kinetics of Connective Tissue Growth Factor Expression during Experimental Proliferative Glomerulonephritis," J. Am. Soc. Nephrol., 12:472-484, (2001).
Jang et al., "Gene Delivery From Polymer Scaffolds for Tissue Engineering," Expert Rev. Medical Devices, 1:127-138, (2004).
Jedsadayanmata et al., "Activation-dependent adhesion of human platelets to Cyr61 and Fispl2/mouse connective tissue growth factor is mediated through integrin alpha(llb)beta(3)" J. Biol. Chem., 274:24321-24327, (1999).
Kasaragod, A.B. et al., "Connective Tissue Growth Factor Expression in Pediatric Myofibroblastic Tumors," Pediatr. Dev. Pathol., 4:37-45, (2001).
Kim et al., "Identification of a family of low-affinity insulin-like growth factor binding proteins ( IGFBPs) : characterization of connective tissue growth factor as a member of the IGFBP superfamily" PNAS, 94:12981-12986, (1997).
Kondo, S. et al., "Characterization of a Mouse ctgf 3'UTR Segment That Mediates Repressive Regulation of Gene Expression," Biochem. Biophys. Res. Commun., 278:119-124, (2000).
Kothapalli, D. et al., "Transforming growth factor beta induces anchorage-independent growth of NRK fibroblasts via a connective tissue growth factor-dependent signaling pathway," Cell Growth Diff., 8:61-68, (1997).
Kryger Z. B., et al., "Mustoe TA. Temporal expression of the transfoming growth factor-Beta pathway in the rabbit ear model of wound healing and scarring," JAm Coll Surg 205(1) :78-88 (1977).
Kubota, S. et al., "Involvement of cis-acting repressive element ( s) in the 3' -untranslated region of human connective tissue growth factor gene," FEBS Lett., 450:84-88, (1999).
Lasky, J.A. et al., "Connective tissue growth factor mRNA expression is unregulated in bleomycin-induced lung fibrosis," Am. J. Physiol., 275:L365-L371, (1998).
Lau, L.F. et al., "The CCN Family of Angiogenic Regulators: The Integrin Connection," Exp. Cell Res., 248:44-57, (1999).
Leask, A. and Abraham, D. J., TGF-beta signaling and the fibrotic response. Faseb J., 18(7) :816-27, (2004).
Lin, C. G., et al., "F. Integrindependent functions of the angiogenic inducer NOV (CCN3) : implication in wound healing," J Biol Chern., 280(9) :8229-37, (2005).
Lopez-Bermejo et al., "Characterization of insulin-like growth factor-binding protein-related proteins (IGFBP-rPs) 1, 2, and 3 in human prostate epithelial cells: potential roles for IGFBP-rPI and 2 in senescence of the prostatic epithelium" Endocrinology, 41:4072-4080, (2000).
Lu et al. "The Temporal Effects of Anti-TGF-JH, 2, and 3 Monoclonal Antibody on Wound Healing and Hypertrophic Scar Formation," J. Am. Coll. Surg., 201:391-397, (2005).

(56) References Cited

OTHER PUBLICATIONS

Martinerie, et al., "Physical mapping of human loci homologous to the chicken nov proto-oncogene," Oncogene, 7:2529-2534 (Abstract only), (1992).

Matveeva et al., "A rapid in vitro method for obtaining RNA accessibility patterns for complementary DNA probes: correlation with an intracellular pattern and known RNA structures" Nucleic Acids Res., 25:5010-5016, (1997).

Milner et al., "Selecting effective antisense reagents on combinatorial oligonucleotide arrays" Nature Biot (1997) 15:537-541.

Moussad, E.A. et al., "Connective Tissue Growth Factor: What's in a Name?" Mol. Genet. Metab., 71:276-292 (2000).

Mustoe, T. A., et al., "Growth factorinduced acceleration of tissue repair through direct and inductive activities in a rabbit dermal ulcer model," J Clin Invest., 87(2) :694-703, (1991).

Mustoe, T. A., "Scars and keloids," BMJ Clinical research ed., 328(7452) :1329-30, (2004).

Nakanishi et al., "Overexpression of connective tissue growth 87. factor/hypertrophic chondrocyte-specific gene products 24 decreases bone density in adult mice and induces dwarfism" Biochem. Biophys. Res. Commun., 281:678-681, (2001).

Office Action issued Apr. 17, 2007 in connection with U.S. Appl. No. 10/946,914.

Office Action issued Dec. 2, 2004 in connection with U.S. Appl. No. 10/006,191.

Office Action issued Feb. 29, 2012 in connection with U.S. Appl. No. 13/329,095.

Office Action issued Jun. 17, 2011 in connection with U.S. Appl. No. 13/007,900.

Office Action issued Mar. 12, 2010 in connection with U.S. Appl. No. 11/985,843.

Office Action issued Mar. 31, 2011 in connection with U.S. Appl. No. 12/547,481.

Office Action issued May 19, 2004 in connection with U.S. Appl. No. 10/006,191.

Office Action issued May 26, 2009 in connection with U.S. Appl. No. 11/985, 843.

Office Action issued Nov. 29, 2011 in connection with U.S. Appl. No. 12/547,481.

Office Action issued Oct. 31, 2007 in connection with U.S. Appl. No. 10/946,914.

Opalinska, et al., "Nucleic-Acid Therapeutics: Basic Principles and Recent Applications" Nature Review, 1:503-514 (2002).

Patzel, et al., "A theoretical approach to select effective antisense oligodeoxyribonucleotides at high statistical probability" Nucleic Acids Res., 27: 4328-4334, (1999).

Patzel, et al., "Theoretical design of antisense RNA structures substantially improves annealing kinetics and efficacy in human cells" Nature Biotech., 16:64-68, (1998).

Pereira et al., "Transcriptional regulation of connective tissue growth factor by cortisol in osteoblasts" Am. J. Physiol. Endocrinol. Metab., 279:E570-E576, (2000).

Perrachi, "Prospects for Anti viral Ribozymes and Deoxyribozymes" Rev. Med. Virol., 14:47-64, (2004).

Preliminary Amendment filed Dec. 9, 2008 in connection with U.S. Appl. No. 12/011,761.

Reid, R. R., et al., "Inhibition of procollagen C-proteinase reduces scar hypertrophy in a rabbit model of cutaneous scarring," Wound Repair Regen, 14(2):138-41, (2006).

Response filed Aug. 15, 2007 in connection with U.S. Appl. No. 10/946,914.

Response filed Feb. 2, 2005 in connection with U.S. Appl. No. 10/006,191.

Response filed Nov. 27, 2009 in connection with U.S. Appl. No. 11/985,843.

Response filed Sep. 20, 2004 in connection with U.S. Appl. No. 10/006,191.

Riser, B.L., et al., "Regulation of connective tissue growth factor activity in cultured rat mesangial cells and its expression in experimental diabetic glomerulosclerosis," J Am Soc Nephrol.,11(1) :25-38, (2000).

Riser et al., "Urinary CCN (CTGF) as a Possible Predictor of Diabetic Nephropathy: Preliminary Report" Kidney International, 64:451-458, (2003).

Santos, et al., "Intraocular Delivery of Oligonucleotides," Curr. Pharm. Biotech., 6:7-15, (2005).

Shi-Wen, X., et al., "Autocrine overexpression of CTGF maintains fibrosis: RDA analysis of fibrosis genes in systemic sclerosis," Exp Cell Res., 259(1) :213-24, (2000).

Shimo, T. et al. "Inhibition of Endogenous Expression of Connective Tissue Growth Factor by Its Antisense Oligonucleotide and Antisense RNA Suppresses Proliferation and Migration of Vascular Endothelial Cells," J. Biochem., 124:130-140, (1998).

Shull, M. M., et al., "Targeted disruption of the mouse transforming growth factor-beta 1 gene results in multifocal inflammatory disease," Nature, 359(6397) :693-9, (1992).

Sisco et al., "Antisense Inhibition of Connective Tissue Growth Factor (CTGF/CCN2} mRNA Limits Hypertrophic Scarring Without Affecting Wound Healing in Vivo," Wound Rep. Reg.,16:661-673, (2008).

Tsubaki, J., et al., "Effects of sodium butyrate on expression of members of the IGF-binding protein superfamily in human mammary epithelial cells," J. Endocrinol., 169:97-110, (2001).

Twigg et al., "Advanced glycosylation end products up-regulate connective tissue growth factor (insulin-like growth factorbinding protein-related protein 2) in human fibroblasts: a potential mechanism for expansion of extracellular matrix in diabetes mellitus" Endocrinology, 142:1760-1769, (2001).

Vorwerk, P. et al., "CTGF (IGFBP-rP2) is specifically expressed in malignant lymphoblasts of patients with acute lymphoblastic leukaemia (ALL)," Brit. J. Cancer, 83:756-760, (2000).

Wahab et al., "Connective tissue growth factor and regulation of the mesangial cell cycle: role in cellular hypertrophy" J. Am. Soc. Nephrol.,13:2437-2445, (2002).

Wahab et al., "Role of connective tissue growth factor in the pathogenesis of diabetic nephropathy" Biochem. J. 359:77-87 (2001).

Walton et al., "Prediction of antisense oligonucleotide binding affinity to a structured RNA target" Biotechnology and Bioengineering (1999) 65:1-9.

Wang, J.F., et al., "Connective tissue growth factor siRNA modulates mRNA levels for a subset of molecules in normal and TGF-beta !-stimulated porcine skin fibroblasts," Wound Repair Regen.,12(2) :205-16 (2004).

Yang, D.H. et al., (1998) Identification of Glycosylated 38-kDa Connective Tissue Growth Factor ( IGFBP-Related Protein 2) and Proteolytic Fragments in Human Biological Fluids, and Up Regulation, ????Page Nos. (1998).

Yokoi, et al., "Role of connective tissue growth factor in fibronectin expression and tubulointerstitial fibrosis" Am. J. Physiol. Renal Physiol., 282:F933-F942, (2002).

Zhang, et al., Reduction of liver Fas expression by an antisense oligonucleotide protects mice from fulminant hepatitis. Nat Biotechnol.,18(8) :862-7, (2000).

Colwell AS, Phan TT, Kong W, Longaker MT, Lorenz PH. Hypertrophic scar fibroblasts have increased connective tissue growth factor expression after transforming growth factor-beta stimulation. Plast Reconstr Surg. 116 (5) :1387-90; discussion 91-2, (2005).

Sisco M, Kryger ZB, Jia SC, Schultz GS, Dean NM, Mustoe TA. Antisense oligonucleotides against transforming growth factorbeta delay wound healing in a rabbit ear model. J Am Coll Surg 2005;201:S60.

Yokoi et al., "Role of connective tissue growth factor in profibrotic action of transforming growth factor-Beta: a potential target for preventing renal fibrosis" Am. J. Kidney Disease (2001) 38(4 Suppl. 1) :SI34-SI38.

Response filed May 29, 2012 in connection with U.S. Appl. No. 12/547,481.

Final Office Action issued Jun. 12, 2012 in connection with U.S. Appl. No. 12/547,481.

Amendment and Request for Continued Examination (RCE) filed Dec. 12, 2012 in connection with U.S. Appl. No. 12/547,481.

FIGURE 3A (hypertrophic scar 24 weeks post revision surgery)
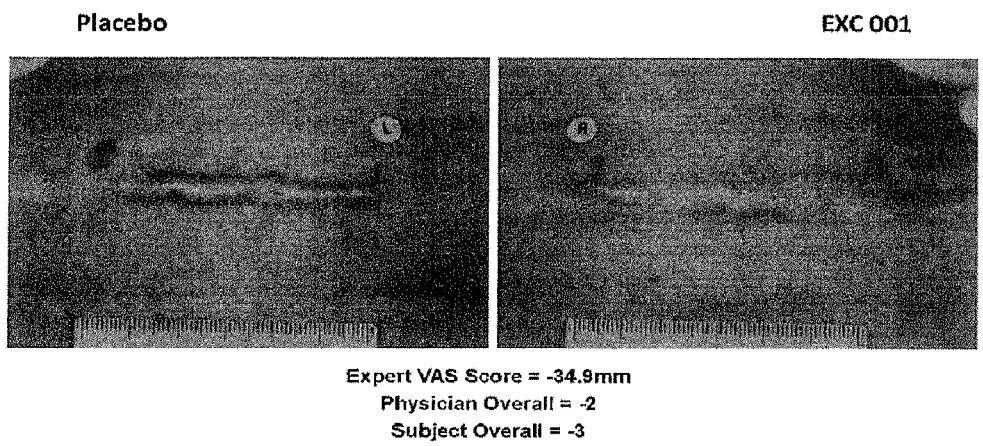
Expert VAS Score = -34.9mm
Physician Overall = -2
Subject Overall = -3
FIGURE 3B (keloid scar 24 weeks post revision surgery)
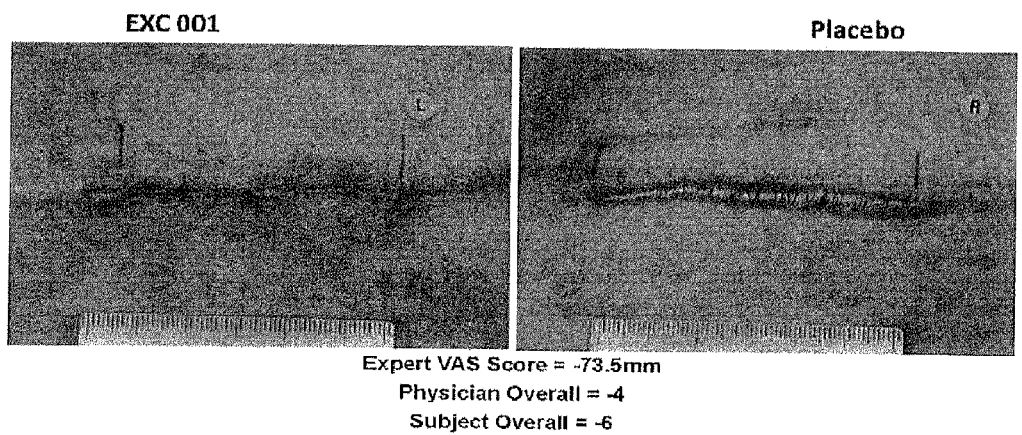
Expert VAS Score = -73.5mm
Physician Overall = -4
Subject Overall = -6

FIGURE 4: Hypertrophic scar 12 weeks post abdominoplasty surgery.
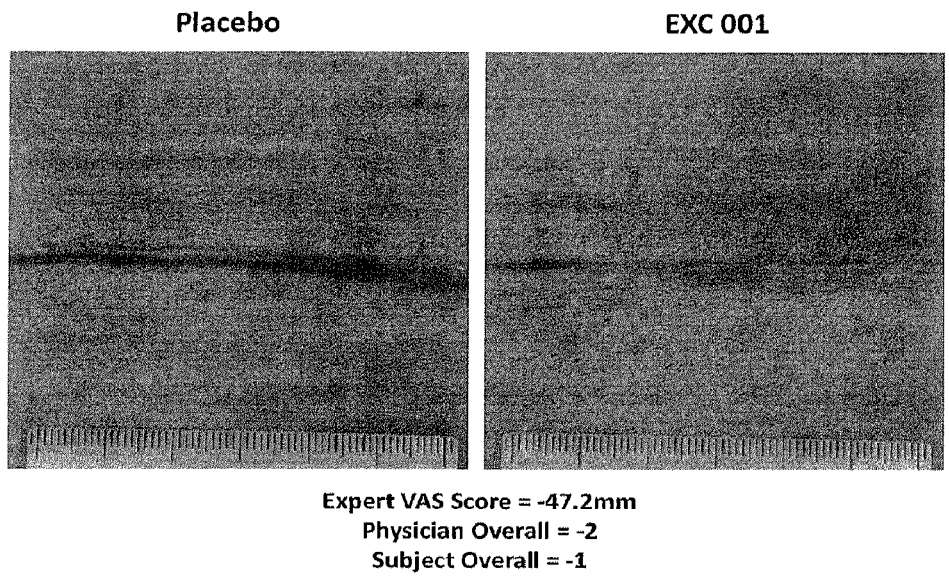
Expert VAS Score = -47.2mm
Physician Overall = -2
Subject Overall = -1

FIGURE 5: Example of limited lateral diffusion of EXC 001 distal to injection site.
Abdominoplasty Study (#202)
Week 12
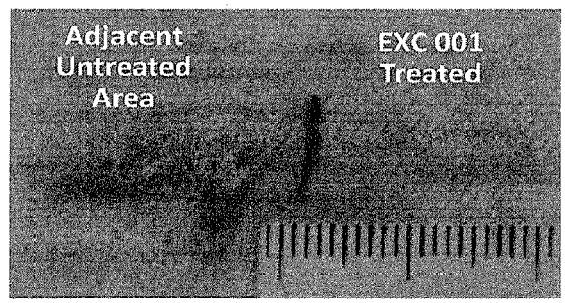

EXC 001 mediated reduction in abdominal scar severity and CTGF protein expression.

CTGF Immunohistochemistry (protein staining)

METHOD OF TREATING KELOIDS OR HYPERTROPHIC SCARS USING ANTISENSE COMPOUNDS TARGETING CONNECTIVE TISSUE GROWTH FACTOR (CTGF)

This application claims the benefit of U.S. Provisional Application No. 61/438,879, filed Feb. 2, 2011; U.S. Provisional Application No. 61/488,666, filed May 20, 2011; and U.S. Provisional Application No. 61/527,821, filed Aug. 26, 2011, the contents of each of which are hereby incorporated in their entireties into this application.

PARTIES TO A JOINT RESEARCH AGREEMENT

The presently claimed invention was made by or on behalf of one or more parties to a joint research agreement that was in effect on or before the effective filing date of the claimed invention, and the claimed invention was made as a result of activities undertaken within the scope of the joint research agreement. The parties to the joint research agreement are ISIS PHARMACEUTICALS, INC., and EXCALIARD PHARMACEUTICALS, INC.

Throughout this application, various patents and publications are referenced. The disclosures of these patents and publications in their entireties are hereby incorporated by reference into this application in order to more fully describe the state of the art to which this invention relates.

FIELD OF INVENTION

This invention concerns methods of preventing formation of, or treating, fibrotic lesions, including skin scars such as keloids and hypertrophic scars.

BACKGROUND OF THE INVENTION

Antisense compounds are an effective means for reducing the expression of specific gene products and may be uniquely useful in a number of therapeutic applications, for example, for the modulation of expression of proteins involved in fibrosis such as connective tissue growth factor (CTGF). (See U.S. Pat. No. 6,965,025B2 to Gaarde et al.)

Antisense compounds are oligomeric compounds that are capable of hybridizing to a target nucleic acid (e.g. a target mRNA molecule) and inhibiting expression of the target nucleic acid.

Antisense compounds, compositions and methods for modulating expression of CTGF and for treating diseases associated with expression of CTGF are disclosed in U.S. Pat. No. 6,965,025B2. However, there remains a need for additional such compounds capable of providing enhanced inhibition of CTGF expression as well as other advantageous properties.

Connective tissue growth factor (CTGF; also known as ctgrofact, fibroblast inducible secreted protein, fisp-12, NOV2, insulin-like growth factor-binding protein-related protein 2, IGFBP-rP2, IGFBP-8, HBGF-0.8, Hcs24, and ecogenin) is a member of the CCN (CTGF/CYR61/NOV) family of modular proteins, named for the first family members identified, connective tissue growth factor, cysteine-rich (CYR61), and nephroblastoma overexpressed (NOV), but the family also includes the proteins ELM-1 (expressed in low-metastatic cells), WISP-3 (Wnt-1-induced secreted protein), and COP-1 (WISP-2). CCN proteins have been found to be secreted, extracellular matrix-associated proteins that regulate cellular processes such as adhesion, migration, mitogenesis, differentiation, survival, angiogenesis, atherosclerosis, chondrogenesis, wound healing, tumorigenesis, and vascular and fibrotic diseases like scleroderma (Lau and Lam, Exp. Cell Res., 1999, 248, 44-57). The connective tissue growth factor protein was shown to stimulate DNA synthesis and promote chemotaxis of fibroblasts (Bradham et al., J. Cell Biol., 1991, 114, 1285-1294).

Connective tissue growth factor is expressed in fibroblasts during normal differentiation processes that involve extracellular matrix (ECM) production and remodeling. Connective tissue growth factor is also frequently overexpressed in fibrotic skin disorders such as systemic sclerosis, localized skin sclerosis, keloids, scar tissue, eosinophilic fasciitis, nodular fasciitis, and Dupuytren's contracture. Connective tissue growth factor mRNA or protein levels are elevated in fibrotic lesions of major organs and tissues including the liver, kidney, lung, cardiovascular system, pancreas, bowel, eye, and gingiva. In mammary, pancreatic and fibrohistiocytic tumors characterized by significant connective tissue involvement, connective tissue growth factor is overexpressed in the stromal compartment.

The Role of CTGF in Keloid Diseases

Keloid disease (KD) is a benign dermal fibro-proliferative tumor characterized by an excessive accumulation of extracellular matrix proteins, leading to an overabundance of collagen formation. Abnormal skin scarring can occur, post-injury in genetically susceptible individuals. KD can also be a familial condition, occurring more commonly in ethnic groups with darker skin. The highest incidence of keloids is found in the black population, where it has been estimated to be around 4-6% and up to 16% in random samples of black Africans. Various modes of inheritance have been proposed for KD ranging from autosomal recessive to autosomal dominant with incomplete clinical penetrance and variable expression. The majority of keloids can lead to considerable cosmetic defects, but can also grow large enough to become symptomatic, by causing deformity or limiting joint mobility.

Although low levels of CTGF are expressed in normal skin, CTGF becomes up-regulated following dermal injury, and it becomes persistently over-expressed when scarring is severe, as in keloids or systemic sclerosis. Fibroblasts cultured from both hypertrophic scars, keloids, and scleroderma lesions express increased basal CTGF (Exp. Cell Res. 2000, 259: 213-224), and cells cultured from hypertrophic scars and keloids were shown to express more CTGF basally and also elaborate more CTGF in response to stimulation with TGF-β (Plast. Reconstr. Surg. 2005, 116: 1387-90). Similarly, transcription of CTGF after serum stimulation was significantly higher in keloid versus normal fibroblasts in cell culture (Ann. Surg. 2007, 246(5):886-95).

In keloid tissue, fibroblasts expressing CTGF mRNA were found distributed throughout the lesions, especially in the peripheral areas (J. Invest. Derm. 1996, 106:729-733). CTGF mRNA expression levels have been compared in normal skin, keloid scars, hypertrophic scars, and mature scars. CTGF mRNA was strongly detected in all cases of the keloids, although not in mature scars. There was a significant difference between levels found in keloids and normal skin (J. Japan Soc. Plastic Reconstr. Surg. 2002, 22:560-565). Recent data also suggests that, relative to normal fibroblasts, keloid scar fibroblasts synthesize 100-150-fold more CTGF in response to exogenous TGF-β1 than do normal fibroblasts (Plast. Reconstr. Surg. 2005, 116:1387-1390). When compared to normal skin, increased localization of CTGF was seen in the basal layer of keloid epidermis and higher expression of CTGF was observed in keloid tissue extract (J. Cell Physiol. 2006, 208(2):336-43). Previously no data has been generated to validate the role of CTGF in keloid disease by showing that inhibition of CTGF expression inhibits keloid growth.

Currently, no effective single therapeutic regimen has been established for treatment of keloids or prevention of keloids growth after surgery. Existing therapeutic approaches include occlusive dressings, compression therapy, intra-lesional steroid injections, cryosurgery, surgical excision, laser treatment, radiation therapy, Kenalog (triamcinolone), interferon therapy, bleomycin, 5-flouracil, verapamil, imiquimod cream, and combinations thereof. Both silicone and non-silicone-based occlusive dressings have been a widely used clinical option for keloids for the last 30 years, but all of these methods result in very limited efficacy and it is widely understood that a new therapy for keloids is urgently needed.

Various forms of radiotherapy have been attempted as a mono-therapy for keloids, but remain quite controversial because of anecdotal reports of carcinogenesis after treatment. Laser therapy using argon, $CO_2$, and pulse dye have been repeatedly attempted during the last 40 years, but none of them have proven to be efficacious. All three forms of laser therapy, according to multiple studies, have recurrence rates of upwards of 90%, showing little to no benefit. Cryotherapy has been used as a mono-therapy. However, side effects associated with this approach include pain at the therapeutic site and hypo- or hyper-pigmentation. Intra-lesional triamcinolone acetone injections, a type of corticosteroid, is frequently used as first-line therapy for the treatment of keloids, but again, actual reported clinical efficacy varies widely. In addition, the need for multiple injections, along with the side effects of injection pain, skin atrophy, telangiectasias, and altered pigmentation have caused clinicians and researchers to continue seeking other means of treatment.

Consequently, there remains a long felt need for additional methods and agents to effectively prevent the formation of keloids, hypertrophic scars, and other types of fibrotic lesions as well as to treat keloids, hypertrophic scars and fibrotic lesion so as to eliminate or reduce them and/or to prevent their reoccurrence. The clinical results described herein clearly demonstrate for the first time the ability of an antisense oligonucleotide targeting CTGF to reduce the growth and severity of keloids post surgery.

Antisense Dosing into Skin

It has also been demonstrated for the first time that antisense oligonucleotides do not diffuse laterally very far after dosing into skin (see Example 2) which could lead to irregular effects of this class of drug on a linear incision/healing scar or keloid if dosing was conducted as a single bolus type of administration, resulting in variable concentrations of antisense along the length of the developing scar. To overcome this drawback, a method for delivering antisense oligonucleotides by an intradermal threading technique has been developed. This technique effectively delivers a constant amount of antisense drug along the full length of the scar, and results in effective and consistent scar reduction along the full length of the scar or keloid.

Intradermal threading consists of introducing a needle into the dermis at an angle as parallel to the skin as possible, and threading the needle into and along the dermis for a distance of typically between 1 and 5 cm. At this point, the needle is withdrawn and drug injected into the dermis along the full length of the needle tract as the needle is withdrawn, resulting in an equal amount and volume of drug being deposited along the full length of the needle tract.

SUMMARY OF THE INVENTION

This invention provides a method for treating a keloid, or preventing the formation, reformation, or growth of a keloid after an injury to the skin, in a subject in need thereof, which comprises administering to the subject by one or more injections at the site of the keloid or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the keloid, wherein the effective amount is from 0.1 to 50 mg of the modified oligonucleotide per injection per linear centimeter of the keloid or of the injury to the skin.

This invention also provides a method for treating a hypertrophic scar, or preventing the formation, reformation, or growth of a hypertrophic scar after an injury to the skin, in a subject in need thereof, which comprises administering to the subject by one or more injections at the site of the hypertrophic scar or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the hypertrophic scar, wherein the effective amount is from 0.1 to 25 mg of the modified oligonucleotide per injection per linear centimeter of the hypertrophic scar or of the injury to the skin.

The invention further provides a method for reducing formation, reformation, or growth of a scar or keloid at a site of an injury to the skin, or of treating a pre-existing scar or keloid, in a subject in need thereof, which comprises administering to the subject by one or more threading injections at the site of the injury or of the pre-existing scar or keloid, a composition which comprises a modified oligonucleotide, or a salt or ester thereof, targeted to a nucleic acid encoding a protein involved in fibrosis in an amount effective to inhibit expression of the protein and thereby reduce scar or keloid formation, reformation, or growth at the site of the injury or to treat the pre-existing scar or keloid.

This invention still further provides a method for reducing formation, reformation, or growth of a fibrotic lesion at a site of an injury, or of treating a pre-existing fibrotic lesion, in a subject in need thereof, which comprises administering to the subject by one or more threading injections at the site of the injury or of the pre-existing fibrotic lesion, a composition which comprises a modified oligonucleotide, or a salt or ester thereof, targeted to a nucleic acid encoding a protein involved in fibrosis in an amount effective to inhibit expression of the protein and thereby reduce formation, reformation, or growth of the fibrotic lesion at the site of the injury or to treat the pre-existing fibrotic lesion.

BRIEF DESCRIPTION OF THE FIGURES

FIG. 3 shows that treatment with a CTGF antisense oligonucleotide, (EXC 001 or SEQ ID NO: 39) inhibits growth of both hypertrophic scars and keloids at 24 weeks post scar revision surgery in humans. The scores below each set of pictures represent the degree of improvement between placebo- and EXC 001-treated keloids. A negative score represents an improvement in scarring resulting from EXC 001 treatment. FIG. 3A show placebo- and EXC 001-treated hypertrophic scars 24 weeks post scar revision surgery. FIG. 3B show placebo- and EXC 001-treated keloid scars 24 weeks post scar revision surgery (described in Example 4).

FIG. 4 shows that treatment with CTGF antisense oligonucleotide, (EXC 001 or SEQ ID NO: 39) inhibits the formation and growth of a hypertrophic scar 12 weeks post abdominoplasty surgery. The scores below the pictures represent the degree of improvement between placebo- and EXC 001-treated scar. A negative score represents an improvement in scarring resulting from EXC 001 treatment (described in Example 5).

FIG. 5 shows the limited diffusion of EXC 001 when dosed adjacent to a scar (described in Example 5). The section of the abdominoplasty scar on the right side of the scar (to the right of the vertical line) was treated with EXC 001 whereas the scar to the left of the vertical line did not receive any treatment. Clearly the scar severity to the right is less than to the left. This example demonstrates that the EXC 001 therapeutic benefit is limited to the region of scar directly adjacent to the site of drug delivery by intradermal threading. Therefore the drug appears to have limited diffusion away from the site of administration and will require dosing immediately adjacent to and along the length of the potential scar site, for example by intradermal threading.

DETAILED DESCRIPTION OF THE INVENTION

Figure 1A:
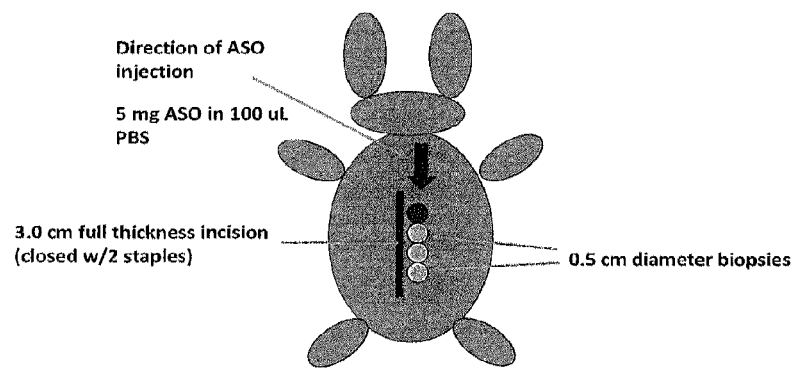
FIG. 1 shows that 2'MOE containing antisense oligonucleotides diffuse over relatively short distances (~0.5-1.0 cm) in rabbit skin when given by intradermal injection (described in Example 2).

This invention provides a method for treating a keloid, or preventing the formation, reformation, or growth of a keloid after an injury to the skin, in a subject in need thereof, which comprises administering to the subject by one or more injections at the site of the keloid or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the keloid, wherein the effective amount is from 0.1 to 50 mg of the modified oligonucleotide per injection per linear centimeter of the keloid or of the injury to the skin.

This invention also provides a method for treating a hypertrophic scar, or preventing the formation, reformation, or growth of a hypertrophic scar after an injury to the skin, in a subject in need thereof, which comprises administering to the subject by one or more injections at the site of the hypertrophic scar or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the hypertrophic scar, wherein the effective amount is from 0.1 to 25 mg of the modified oligonucleotide per injection per linear centimeter of the hypertrophic scar or of the injury to the skin.

This invention further provides a method for reducing formation, reformation, or growth of a scar or keloid at a site of an injury to the skin, or of treating a pre-existing scar or keloid, in a subject in need thereof, which comprises administering to the subject by one or more threading injections at the site of the injury or of the pre-existing scar or keloid, a composition which comprises a modified oligonucleotide, or a salt or ester thereof, targeted to a nucleic acid encoding a protein involved in fibrosis in an amount effective to inhibit expression of the protein and thereby reduce scar or keloid formation, reformation, or growth at the site of the injury or of treat the pre-existing scar or keloid. This invention still further provides a method for reducing formation, reformation, or growth of a fibrotic lesion at a site of an injury, or of treating a pre-existing fibrotic lesion, in a subject in need thereof, which comprises administering to the subject by one or more threading injections at the site of the injury or of the pre-existing fibrotic lesion, a composition which comprises a modified oligonucleotide, or a salt or ester thereof, targeted to a nucleic acid encoding a protein involved in fibrosis in an amount effective to inhibit expression of the protein and thereby reduce formation, reformation, or growth of the fibrotic lesion at the site of the injury or to treat the pre-existing fibrotic lesion.

In one embodiment of the preceding methods, the one or more threading injections comprise multiple intradermal threading injections per scar.

In the preceding methods, the protein involved in fibrosis may be connective tissue growth factor, transforming growth factor beta-1, mothers against decapentaplegic homolog-3, early growth response-1, monocyte chemotactic protein-1, a collagen, or an elastin. Examples of suitable collagens are Collagen 3A1, Collagen 1A2, and Collagen 1A1.

In certain embodiments of the methods of this invention, the effective amount is from 0.1 to 50 mg, e.g. 0.1 to 25 mg, of the modified oligonucleotide per injection per linear centimeter of the site of the injury to the skin or of the pre-existing scar.

In certain embodiments, the modified oligonucleotide is administered at least once every two weeks for at least four weeks, i.e. at least twice.

In other embodiments, the modified oligonucleotide is administered at least once every three weeks for at least six weeks, i.e. at least twice.

In still other embodiments, the modified oligonucleotide is administered at least once every four weeks for at least eight weeks. In yet other embodiments, the modified oligonucleotide is administered at least once every eight weeks for at least sixteen weeks.

It is currently contemplated that it may be preferable that the modified oligonucleotide is administered over a period of at least nine weeks, for example over a period of 26 weeks.

In certain embodiments, the modified oligonucleotide consists of 12-30 linked nucleosides, at least a 12 nucleobase sequence portion of which is present within a region selected from the group consisting of nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129, and 1399-1423 of SEQ ID NO: 9.

In certain embodiments, at least a 12 nucleobase sequence portion of the modified oligonucleotide is present within the nucleobase sequence set forth in any of the sequences set forth in SEQ ID NO: 28, 30, 39, 40, 43, 44, 45, 50, 51, 52, 56, 78, 125, or 166.

In certain embodiments, the modified oligonucleotide consists of at least 14, e.g. 20, linked nucleosides.

In certain embodiments, the modified oligonucleotide is a single-stranded oligonucleotide. In others, the modified oligonucleotide is a double-stranded oligonucleotide.

In still other embodiments, the modified oligonucleotide comprises at least one oligodeoxyribonucleotide or at least one oligoribonucleotide.

In certain embodiments, the modified oligonucleotide has a sequence which is 100% identical over its length to a portion of any one of the sequences set forth in SEQ ID NO: 28, 30, 39, 40, 43, 44, 45, 50, 51, 52, 56, 78, 125, or 166.

In certain embodiments, the modified oligonucleotide comprises at least one modified internucleoside linkage, e.g. a phosphothioate internucleoside linkage, such that some or all of the internucleoside linkages may be phosphothioate internucleoside linkages.

In certain embodiments, at least one nucleoside in the modified oligonucleotide comprises a modified sugar, such as a bicyclic sugar. In some such embodiments, at least one of the modified sugar comprises a 2'-O-methoxyethyl.

In other embodiments, the modified oligonucleotide comprises at least one tetrahydropyran modified nucleoside wherein a tetrahydropyran ring replaces the furanose ring.

In some such embodiments, each of the at least one tetrahydropyran modified nucleoside has the structure:

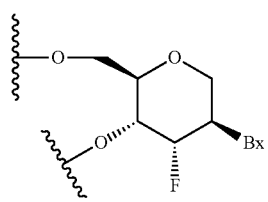

wherein Bx is an optionally protected heterocyclic base moiety.

In certain embodiments, at least one nucleoside comprises a modified nucleobase, e.g. a modified deoxynucleoside, a ribonucleoside, or a 5'-methylcytosine.

In certain embodiments, the modified oligonucleotide comprises:
(a) a gap segment consisting of linked deoxynucleosides;
(b) a 5' wing segment consisting of linked modified nucleosides; and
(c) a 3' wing segment consisting of linked modified nucleosides;
wherein the gap segment is positioned between the 5° wing segment and the 3' wing segment and wherein each modified nucleoside within each wing segment comprises a modified sugar.

In certain currently preferred embodiments, the modified oligonucleotide comprises:
(a) a gap segment consisting of thirteen linked deoxynucleosides;
(b) a 5' wing segment consisting of two linked modified nucleosides; and
(c) a 3' wing segment consisting of five linked modified nucleosides;
wherein the gap segment is positioned between the 5' wing segment and the 3' wing segment, wherein each modified nucleoside within each wing segment comprises a 2'-O-methoxyethyl sugar; and wherein each internucleoside linkage is a phosphothioate linkage.

In certain embodiments, the sequence of the nucleobase is the sequences set forth in SEQ ID NO: 39.

In other embodiments, the sequence of the nucleobase is the sequences set forth in SEQ ID NO: 40.

In still other embodiments, the sequence of the nucleobase is the sequences set forth in SEQ ID NO: 45.

In yet other embodiments, the sequence of the nucleobase is the sequences set forth in SEQ ID NO: 52.

In yet other embodiments, the sequence of the nucleobase is the sequences set forth in SEQ ID NO: 166.

In certain embodiments, the composition comprises the modified oligonucleotide or a salt thereof, and a pharmaceutically acceptable carrier or diluent.

In certain embodiments, the modified oligonucleotide directly or indirectly inhibits expression of collagen or elastin or both, so as to treat the keloid, prevent the formation, reformation, or growth of the keloid, treat the hypertrophic scar, prevent the formation, reformation, or growth of the hypertrophic scar, reduce scar formation at the site of the injury, treat the pre-existing scar, reduce formation of the fibrotic lesion at the site of the injury, or treat the pre-existing fibrotic lesion.

It is currently contemplated that the preceding methods further comprise administering to the subject a second compound.

In certain embodiments, the second compound may be an antisense compound targeting the same or a different sequence, and the modified oligonucleotide and the second compound may be administered simultaneously or sequentially.

In certain embodiments, the modified oligonucleotide is present in a conjugate with a moiety which enhances uptake of the compound into, and/or increases residence time of the compound in, the subject, wherein the residence time is preferably 7 to 60 days. The conjugate moiety is polyethylene glycol, hyaluronic acid, cholesterol, adamantine acetic acid, 1-pyrene butyric acid, dihydrotestosterone, 1,3-Bis-O-(hexadecyl)glycerol, hexadecylglycerol, hexadecylamine, geranyloxyhexyl, palmitic acid, myristic acid, spermine, spermidine, folic acid, vitamin E, a carbohydrate cluster, a peptide (including antennapedia helix, HIV Tat fragments, integrin binding peptide), transportin, or porphyrin.

In certain embodiments, the modified oligonucleotide is administered in a delivery system which enhances uptake of the compound into, and/or increases residence time of the compound in, the subject, wherein the residence time is preferably 7 to 60 days. The delivery system comprises a cationic lipid, a liposome, a microparticle, a nanoparticle, a liquid formulation with suspended particles with or without drug in the solution for immediate release or with drug depot in particles (particularly PLGA and poly-Arg particles), a liquid formulation that gels after injections such as thermosetting/responsive liquids (e.g. pluronic gels), liquids that contain a polymer and drug in a biocompatible solvent that precipitate when the solvent is diluted by body fluids (e.g. atrigel), a gel, a semi-solid formulation such as hydrogel (with a matrix backing or as a spray solution), a powder to be sprinkled on during surgery, a resorbable suture, or a fast dissolving gel or polymer strip.

In certain embodiments, the modified oligonucleotide is administered to the subject following a surgical excision of the keloid, scar, or fibrotic lesion.

In certain embodiments, the injury to the skin is the result of a surgical incision, a biopsy, a skin piercing, a skin removal, a burn, or a wound.

In certain embodiments, the effective amount is about 5 mg of the modified oligonucleotide per injection per linear centimeter of the keloid, the hypertrophic scar, the injury to the skin, the site of the injury, the pre-existing scar, or the pre-existing fibrotic lesion.

In certain embodiments, the modified oligonucleotide is administered for up to 6 months. In other embodiments, the modified oligonucleotide is administered for up to 1 year.

In certain embodiments, the preceding methods further comprise administering to the subject another therapeutic agent which may be a steroid, a silicone wrap, TGF-β3 (i.e. Juvista), collagenase (i.e. Xyflex), 17β-estrodiol (i.e. Zesteem), IL-10 (i.e. Prevascar), mannose 6-phosphate (i.e. Juvidex), a smooth muscle relaxant (i.e. AZX100, a 24-amino acid synthetic peptide), a stem cell therapy (i.e. GBT009), serum amyloid protein, antibodies targeting integrin αvβ6, CTGF, TGFβ, or molecules that inhibit the activity of ALK-4 and/or ALK-5 (the TGF beta receptors), any inhibitor designed to block TNF activity (for example etanercept), occlusive dressings, compression therapy, cryosurgery, surgical excision, laser treatment, radiation therapy, interferon therapy, bleomycin, 5-fluorouracil, verapamil, imiquimod cream, one capable of promoting wound healing, such as Dermagraft, Apligraf, PDGF (i.e. Regranex), electrical stimulation, "growth factors" as a category, dressings as a category, small intestinal submucosa (SIS), Promogran, hyperbaric oxygen, or combinations thereof.

In certain embodiments, the modified oligonucleotide is administered by means of a formulation, ultrasound, electroporation, iontophoresis or micro-needle.

In certain embodiments, the modified oligonucleotide is administered adjacent to the keloid, the hypertrophic scar, the injury to the skin, the site of the injury, the pre-existing scar, or the pre-existing fibrotic lesion.

In other embodiments, the modified oligonucleotide is administered along the entire length of the keloid, the hypertrophic scar, the injury to the skin, the site of the injury, the pre-existing scar, or the pre-existing fibrotic lesion.

In still other embodiments, the modified oligonucleotide is administered along each side of the keloid, the hypertrophic scar, the injury to the skin, the site of the injury, the pre-existing scar, or the pre-existing fibrotic lesion.

In yet other embodiments, the modified oligonucleotide is administered directly into the keloid, the hypertrophic scar, the injury to the skin, the site of the injury, the pre-existing scar, or the pre-existing fibrotic lesion.

In certain embodiments, the subject is genetically predisposed to formation of keloids or hypertrophic scars or both.

In certain embodiments, the modified oligonucleotide is administered intradermally.

In other embodiments, the modified oligonucleotide is administered intradermally by threading technique.

In still other embodiments, the modified oligonucleotide is administered sub-cutaneously.

In yet other embodiments, the modified oligonucleotide is administered topically.

This invention also provides a kit which comprises:
  a. a device pre-filled with the composition comprising the modified oligonucleotide; and
  b. instruction for uses.

In a certain embodiment the antisense oligonucleotide is complementary to a portion of the region of CTGF targeted by active oligonucleotides which stretches from target sites 1396 through 1424. This is the sequence space targeted by oligo 418899, 412295 and 412294/EXC 001(SEQ ID NOs: 166, 40 and 39, respectively).

This invention also provides a modified oligonucleotide comprising at least 12, preferably at least 14, linked nucleosides, the nucleobase sequence of which is a portion of one of the nucleobase sequences set forth in SEQ ID NOs: 28, 30, 39, 40, 43, 44, 45, 50, 51, 52, 56, 78, 125 and 166.

The antisense compounds described herein can comprise an oligonucleotide having 12 to 30, 12 to 20, and preferably 14 to 20 linked nucleosides.

In one embodiment of the invention, the modified oligonucleotide is a single-stranded or a double-stranded oligonucleotide.

The present invention employs oligomeric compounds, particularly antisense oligonucleotides, for use in modulating the function of nucleic acid molecules encoding proteins involved in fibrosis, ultimately modulating the amount of protein produced. This is accomplished by providing antisense compounds which specifically hybridize with one or more nucleic acids encoding a protein involved in fibrosis. As used herein, the terms "target nucleic acid" and "nucleic acid encoding connective tissue growth factor" encompass DNA encoding a protein involved in fibrosis, RNA (including pre-mRNA and mRNA) transcribed from such DNA, and also cDNA derived from such RNA.

The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of connective tissue growth factor. In the context of the present invention, "modulation" means either an increase (stimulation) or a decrease (inhibition) in the expression of a gene. In the context of the present invention, inhibition is the preferred form of modulation of gene expression and mRNA is a preferred target.

Target Nucleic Acids, Target Regions and Nucleotide Sequences

It is preferred to target specific nucleic acids for antisense. "Targeting" an antisense compound to a particular nucleic acid, in the context of this invention, is a multistep process.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In one embodiment, a target region is a structurally defined region of the nucleic acid. For example, a target region may encompass a 3' UTR, a 5' UTR, an exon, an intron, a coding region, a translation initiation region, translation termination region, or other defined nucleic acid region. The structurally defined regions for the nucleic acid can be obtained by accession number from sequence databases such as NCBI and such information is incorporated herein by reference. In other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In other embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In one embodiment, target segments within a target region are separated by no more than about 300 nucleotides. In other embodiments, target segments within a target region are separated by no more than about, 250, 200, 150, 100, 90, 80, 70, 60, 50, 40, 30, 20, or 10 nucleotides on the target nucleic acid. In another embodiment, target segments within a target region are separated by no more than about 5 nucleotides on the target nucleic acid. In additional embodiments, target segments are contiguous.

Suitable target segments may be found within a 5' UTR, a coding region, a 3' UTR, an intron, or an exon. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In one embodiment, reductions in CTGF mRNA levels are indicative of inhibition of CTGF expression. Reductions in levels of a CTGF protein are also indicative of inhibition of target mRNA expression. Further, phenotypic changes are indicative of inhibition of CTGF expression.

Antisense Compounds

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics.

Antisense compound means an oligomeric compound capable of undergoing hybridization to a target nucleic acid through hydrogen bonding. Antisense compounds include, but are not limited to oligonucleotides, oligonucleosides, oligonucleotide analogs, oligonucleotide mimetics, antisense oligonucleotides, siRNA, RNAi, ribozymes, external guide sequence (EGS) oligonucleotides (oligozymes), and other oligonucleotides which hybridize to the target nucleic acid and modulate its expression.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a nucleic acid is 12 to 30 subunits in length. In other words, antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In one preferred embodiment of the invention, the compound comprises 20 or at least 14 linked nucleosides, wherein the modified oligonucleotide has a sequence which is 100% identical to one of the sequences set forth in SEQ ID NOs: 28, 30, 39, 40, 45, 52, 56, 78, 125 and 166. In another preferred embodiment, the lead compound of interest has the sequence set forth in SEQ ID No: 39 (ISIS 412294).

In certain embodiments, a shortened or truncated antisense compound targeted to a nucleic acid has a single subunit deleted from the 5' end (5' truncation), or alternatively from the 3' end (3' truncation). A shortened or truncated antisense compound targeted to a nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two are more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Bhanot et al. (PCT/US2007/068401) provided short antisense compounds, including compounds comprising chemically-modified high-affinity monomers 8 to 16 monomers in length. These short antisense compounds were shown to be useful for reducing target nucleic acids and/or proteins in cells, tissues, and animals with increased potency and improved therapeutic index. Short antisense compounds were effective at lower doses than previously described antisense compounds, allowing for a reduction in toxicity and cost of treatment. In addition, the described short antisense compounds have greater potential for oral dosing.

Hybridizations

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds.

Identity

The antisense compounds provided herein may also have a defined percent identity to a particular nucleotide sequence, SEQ ID NO, or compound represented by a specific oligo (Isis) number. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

In a certain embodiment of the invention, modifications to antisense compounds encompass substitutions or changes to internucleoside linkages, sugar moieties, or nucleobases.

In one embodiment of the invention the compound comprises at least one modification selected from the group consisting of a modified internucleoside linkage, a modified sugar, and a modified nucleobase.

Although antisense oligonucleotides containing a variety of modified internucleoside linkages may be employed, the currently preferred modified internucleoside linkage is a phosphothioate linkage between one or more of the nucleosides or wherein all of the internucleoside linkages are phosphothioate internucleoside linkages.

In general, it is also preferred that the antisense oligonucleotide contains at least one and typically more than one modified sugar, wherein the sugar is a bicyclic sugar. Although various modified sugars may be employed it is presently preferred to employ a 2'-O-methoxyethyl sugar.

Further, at least one and typically more than one of the nucleobases contained in the antisense oligonucleotide will be a modified nucleotide such as a 5-methylcytosine.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleotide Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, antisense compounds targeted to a CTGF nucleic acid comprise one or more modified internucleoside linkages. In some embodiments, the modified internucleoside linkages are phosphorothioate linkages. In other embodiments, each internucleoside linkage of an antisense compound is a phosphorothioate internucleoside linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound.

In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5° to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat.

No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugar Moieties

Modified oligonucleotides may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845 to Seth et al., hereby incorporated by reference herein in its entirety. Other examples of BNAs are described in published International Patent Application No. WO 2007/146511, hereby incorporated by reference herein in its entirety.

Antisense compounds of the invention can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O(CH2)2-OCH3 (2'-O-methoxyethyl or 2'-MOE) substituent group; and bicyclic modified sugars (BNAs), having a 4'-(CH2)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

In some embodiments, the bicyclic sugar moiety is bridged between the 2' and 4' carbon atoms with a biradical group selected from —O—(CH$_2$)p-, —O—CH$_2$—, —O—CH$_2$CH$_2$—, —O—CH(alkyl)-, —NH—(CH$_2$)p-, —N(alkyl)-(CH$_2$)p-, —O—CH(alkyl)-, —(CH(alkyl))—(CH$_2$)p-, —NH—O—(CH$_2$)p-, —N(alkyl)-O—(CH$_2$)p-, or —O—N(alkyl)-(CH$_2$)p-, wherein p is 1, 2, 3, 4 or 5 and each alkyl group can be further substituted. In certain embodiments, p is 1, 2 or 3.

In one aspect, each of said bridges is, independently, —[C(R1)(R2)]n-, —[(C(R1)(R2)]n-O—, —C(R1R2)-N(R1)-O— or —C(R1R2)-O—N(R1)-. In another aspect, each of said bridges is, independently, 4'-(CH$_2$)$_3$-2', 4'-(CH$_2$)$_2$-2', 4'-(CH$_2$)$_2$—O-2', 4'-CH$_2$—O—N(R1)-2' and 4'-CH$_2$—N(R1)-O-2'- wherein each R1 is, independently, H, a protecting group or C1-C12 alkyl.

In nucleotides having modified sugar moieties, the nucleobase moieties (natural, modified or a combination thereof) are maintained for hybridization with an appropriate nucleic acid target.

In one embodiment, antisense compounds targeted to a nucleic acid comprise one or more nucleotides having modified sugar moieties. In a preferred embodiment, the modified sugar moiety is 2'-MOE. In other embodiments, the 2'-MOE modified nucleotides are arranged in a gapmer motif.

Currently preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$. A further preferred modification includes bicyclic nucleic acid (also referred to as locked nucleic acids (LNAs)) in which the 2'-hydroxyl group is linked to the 3' or 4' carbon atom of the sugar ring thereby forming a bicyclic sugar moiety. The linkage is preferably a methylene (—CH$_2$—)$_n$ group bridging the 2' oxygen atom and the 4' carbon atom wherein n is 1 or 2 including a-L-Methyleneoxy (4'-CH2-O-2') BNA, β-D-Methyleneoxy (4'-CH2-O-2') BNA and Ethyleneoxy (4'-(CH2)$_2$-O-2') BNA. Bicyclic modified sugars also include (6'S)-6' methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C, 4'-C-oxymethylene linkage thereby forming a bicyclic sugar moiety. The linkage may be a methylene (—$CH_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Other preferred bridge groups include the 2'-deoxy-2'-$CH_2OCH_2$-4' bridge. LNAs and preparation thereof are described in published International Patent Application Nos. WO 98/39352 and WO 99/14226.

Other preferred modifications include 2'-methoxy (2'-O—$CH_3$), 2'-aminopropoxy (2-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics or surrogates (sometimes referred to as DNA analogs) such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety. In certain embodiments, nucleosides are modified by replacement of the ribosyl ring with a surrogate ring system such as a morpholino ring, a cyclohexenyl ring, a cyclohexyl ring or a tetrahydropyranyl ring such as one having one of the formulae:

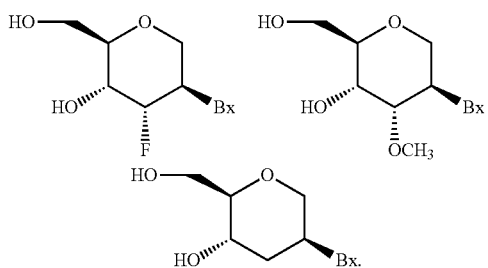

Many other bicyclo and tricyclo sugar surrogate ring systems are also know in the art that can be used to modify nucleosides for incorporation into antisense compounds (see for example review article: Leumann, Christian J.,). Such ring systems can undergo various additional substitutions to enhance activity.

In one embodiment of the invention, the compound comprising at least one tetrahydropyran modified nucleoside wherein a tetrahydropyran ring replaces the furanose ring.

In another embodiment of the invention, wherein each of the at least one tetrahydropyran modified nucleoside has the structure:

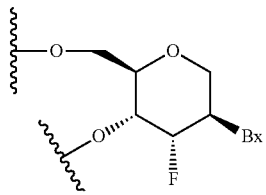

wherein Bx is an optionally protected heterocyclic base moiety.

Modified Nucleobases

Oligonucleotides may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In one embodiment, antisense compounds targeted to a CTGF nucleic acid comprise one or more modified nucleobases. In an additional embodiment, gap-widened antisense oligonucleotides targeted to a CTGF nucleic acid comprise one or more modified nucleobases. In some embodiments, the modified nucleobase is 5-methylcytosine. In further embodiments, each cytosine is a 5-methylcytosine.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which has an owner in common with the owners of the instant application and also herein incorporated by reference.

Antisense Compound Motifs

In certain embodiment of the invention, the compound comprises a modified oligonucleotide comprised of (a) a gap segment consisting of linked deoxynucleosides, preferably consists of a thirteen linked modified deoxynucleosides; (b) a 5' wing segment consisting of linked modified nucleosides, preferably consists of two linked modified nucleosides; and (c) a 3' wing segment consisting of linked modified nucleosides, preferably consists of five linked nucleosides; wherein the gap segment is positioned between the 5' wing segment and the 3' wing segment, and wherein each modified nucleoside within each wing segment comprises a modified sugar, preferably comprises a 2'-O-methoxyethyl sugar; and wherein each internucleoside linkage is a phosphothioate linkage.

These patterns of modified nucleotides in an antisense compound are called motif. These motifs, confer to the antisense compounds properties such to enhance the inhibitory activity, increase binding affinity for a target nucleic acid, or increase resistance to degradation by in vivo nucleases.

In certain embodiments, antisense compounds targeted to a CTGF nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In a preferred embodiment, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 2-13-5, 5-10-5, 4-8-4, 4-12-3, 4-12-4, 3-14-3, 2-16-2, 1-18-1, 3-10-3, 2-10-2, 1-10-1 or 2-8-2.

In some embodiments, the antisense compound as a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10 or 8-2.

In one embodiment, antisense compounds targeted to a nucleic acid possess a 2-13-5 gapmer motif.

In some embodiments, an antisense compound targeted to a CTGF nucleic acid has a gap-widened motif. In other embodiments, an antisense oligonucleotide targeted to a CTGF nucleic acid has a gap-widened motif.

In one embodiment, a gap-widened antisense oligonucleotide targeted to a CTGF nucleic acid has a gap segment of fourteen 2'-deoxyribonucleotides positioned between wing segments of three chemically modified nucleosides. In one embodiment, the chemical modification comprises a 2'-sugar modification. In another embodiment, the chemical modification comprises a 2'-MOE sugar modification.

Antisense compounds having a gapmer motif are considered "chimeric" antisense compounds or "chimeras," which contain two or more chemically distinct regions, each made up of at least one monomer unit, i.e., a nucleotide in the case of an oligonucleotide compound. These oligonucleotides typically contain at least one region modified so as to confer increased resistance to nuclease degradation, increased cellular uptake, increased binding affinity for the target nucleic acid, and/or increased inhibitory activity. It is not necessary for all positions in a given compound to be uniformly modified, and in fact more than one of the aforementioned modifications may be incorporated in a single compound or even at a single nucleoside within an oligonucleotide.

An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

In the case of an antisense oligonucleotide having a gapmer motif, the gap segment generally serves as the substrate for endonuclease cleavage, while the wing segments comprise modified nucleosides. In a preferred embodiment, the regions of a gapmer are differentiated by the types of sugar moieties comprising each distinct region. The types of sugar moieties that are used to differentiate the regions of a gapmer may include β-D-ribonucleosides, β-D-deoxyribonucleosides, 2'-modified nucleosides (such 2'-modified nucleosides may include 2'-MOE), and bicyclic sugar modified nucleosides.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

In another embodiment of the invention, the compound comprises the modified oligonucleotide consists of 20 linked nucleosides.

In a preferred embodiment of the invention, the compound comprises the nucleobase sequence is the sequence set forth in SEQ ID NOs: 39, 40, 45, 52 and 166.

In one embodiment of the invention the composition comprises a modified oligonucleotide comprising linked nucleosides, the nucleobase sequence of which is a sequence set forth in one of SEQ ID NOs: 28, 30, 39, 40, 43, 44, 45, 50, 51, 52, 56, 78, 125 and 166 or a salt thereof, and a pharmaceutically acceptable carrier or diluent. Examples of pharmaceutically acceptable salts are well known to those skilled in the art.

In one embodiment of the invention, the antisense compound is complementary within a range of nucleotides on the CTGF sequence. In certain embodiments the antisense compound is complementary within the range of nucleotides 718-751, 1388-1423, 1457-1689, 2040-2069, 2120-2147, or 2267-2301 of SEQ ID NO: 9. In a certain embodiment the antisense compound is complementary within the range of nucleotides 2728-2797 of SEQ ID NO: 10. Compounds targeted to these ranges demonstrate at least 50% inhibition (i.e. SEQ ID NOs: 15, 29, 31, 42, 46-49, 53, 72, 81, 82, 152-154, 164, and 165). Certain target sites listed in Table 1 also demonstrate at least 50% inhibition (i.e. SEQ ID NOs: 12, 20, 33, 34, 76, 107, 129, 132, 134, 136, and 146). In certain embodiments the antisense compound is complementary within the range of nucleotides 553-611, 1394-1423, 1469-1508, 1559-1605, 1659-1689 or 2100-2129 of SEQ ID NO: 9 and 2623-2647 of SEQ ID NO: 10. Compounds targeted therein demonstrate at least 60% inhibition (i.e. SEQ ID NOs: 27, 28, 38, 39, 40, 43, 44, 45, 50, 51, 52, 54, 55, 56, 77, 78, 79, 138 and 139). Certain additional target sites listed in Table 1 also demonstrate at least 60% inhibition (i.e. SEQ ID NOs: 24, 30, 61, 63, 67, 69, 73, 86, 125, 128, and 161). In certain embodiments the antisense compound is complementary within the range of nucleotides 1399-1423. Compounds targeted therein demonstrate at least 70% inhibition (i.e. SEQ ID NOs: 39 and 40). Certain target sites listed in Table 1 also demonstrate at least 70% inhibition (i.e. SEQ ID NOs: 28, 30, 44, 45, 51, 56, 78, 128, and 138). One target site listed in Table 1 also demonstrates at least 80% inhibition (i.e. SEQ ID NO: 44). In certain embodiments, the percent inhibition is achieved when the antisense compound is delivered to HuVec cells at a concentration of 50 nm. Refer to Example 8, provided herein below, for more details.

In an embodiment of the composition, the modified oligonucleotide is a single-stranded or double stranded oligonucleotide. In another embodiment of the invention, comprising a modified oligonucleotide, wherein the modified oligonucleotide consists of 20 linked nucleosides In another embodiment of the invention, provides a method for inhibiting expression of connective tissue growth factor in a cell or a tissue which comprises contacting the cell or tissue with the compound of interest under conditions such that expression of connective tissue growth factor is inhibited.

Antisense oligonucleotides may be combined with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a nucleic acid and a pharmaceutically acceptable diluent. In one embodiment, the pharmaceutically acceptable diluent is PBS. In another embodiment, the pharmaceutically acceptable diluent is pharmaceutical grade saline or pharmaceutical grade PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

In certain embodiment of the invention, a pharmaceutically acceptable carrier or diluent is an ingredient in a composition that lacks pharmacological activity, but is pharmaceutically necessary or desirable as a solvent, suspending agent or any other pharmaceutically inert vehicle for delivering one or more nucleic acids to a human or non-human animal. Pharmaceutical carriers are well known to those skilled in the art.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which does not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

In one embodiment of the invention, the composition comprises a modified oligonucleotide comprises a single-stranded or a double-stranded oligonucleotide, and wherein the modified oligonucleotide consists of 20 linked nucleosides.

In another embodiment of the invention involves a method for inhibiting expression of connective tissue growth factor in a cell or a tissue which comprises contacting the cell or tissue with any one of the above-mentioned compounds under conditions such that expression of connective tissue growth factor is inhibited.

In certain embodiment of the invention involves a method of treating an animal having a disease or condition associated with expression of connective tissue growth factor which comprises administering to the animal an amount of the compound described hereinabove effective to inhibit expression of connective tissue growth factor so as to thereby treat the animal.

In the practice of the method of this invention, an animal includes a human as well as a non-human animal, preferably human.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be by intradermal administration, including intradermal threading of the injection needle, sub-cutaneous, topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred intradermal and topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, syringes, pre-filed syringes, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethyl-cellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245).

Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for intradermal and topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEES Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}$ 15G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al.

discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).
Penetration Enhancers In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.
Surfactants:

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).
Fatty Acids:

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).
Bile Salts:

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxy-cholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents:

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-Chelating Non-Surfactants:

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids into and through the skin, including glycols such as ethylene glycol and propylene glycol, pyrrols such as 2-pyrrol, azones, and terpenes such as limonene and menthone.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The antisense compounds used in accordance with this invention may be conveniently and routinely made through the well-known technique of solid phase synthesis. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Certain Indications

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In one embodiment of the invention the method comprises treating a disease or condition, wherein the disease or disorder is a fibrotic disease. In one embodiment of the method of the invention, the fibrotic disease is hypertrophic scarring, keloids, skin scarring, liver fibrosis, pulmonary fibrosis, renal fibrosis, cardiac fibrosis, or restenosis.

In another embodiment of the invention, the method further comprises treating the above-mentioned disease or condition, wherein the disease or disorder is joint fibrosis (including frozen shoulder syndrome, tendon and peripheral nerve damage), surgical adhesions, spinal cord damage, coronary bypass, abdominal and peritoneal adhesions (including endometriosis, uterine leiomyomata and fibroids), radial keratotomy and photorefractive keratectomy, retinal reattachment surgery, device mediated fibrosis (in for example diabetes), tendon adhesions, Dupuytren contracture, or scleroderma.

In another embodiment of the invention also provides a method for reducing hypertropic scarring or keloids resulting from dermal wound healing in a subject in need thereof which comprises administering to the subject an amount of compound of an antisense oligonucleotide effective to inhibit expression of connective tissue growth factor (CTGF) in the subject so as to thereby reduce scarring.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. In general, dosage from 0.1 to 25 mg per injection per linear cm of scar is used, and may be given daily, weekly, every 3 weeks, monthly or bi-monthly.

In another embodiment of this invention, the method further comprises reducing hypertropic scarring or keloids resulting from dermal wound healing, wherein wound healing is healing at a wound selected from the group consisting of skin breakage, surgical incisions and burns.

In certain embodiments, the invention provides methods of treating an individual comprising administering one or more pharmaceutical compositions of the present invention. In certain embodiments, the individual has one of the above mentioned disorders. In certain embodiments, the individual is at risk for one of the above mentioned disorders. In certain embodiments, the individual has been identified as in need of therapy. In certain embodiments the invention provides methods for prophylactically reducing CTGF expression in an individual.

Certain embodiments include treating an individual in need thereof by administering to an individual a therapeutically effective amount of an antisense compound targeted to a CTGF nucleic acid.

In one embodiment, administration of a therapeutically effective amount of an antisense compound targeted to a CTGF nucleic acid is accompanied by monitoring of CTGF levels in the skin and/or serum of an individual, to determine an individual's response to administration of the antisense compound. An individual's response to administration of the antisense compound is used by a physician to determine the amount and duration of therapeutic intervention.

In one embodiment, administration of an antisense compound targeted to a CTGF nucleic acid results in reduction of CTGF expression by at least 15, 20, 25, 30, 35, 40, 45, 50, 55, 60, 65, 70, 75, 80, 85, 90, 95 or 99%, or a range defined by any two of these values. In one embodiment, administration of an antisense compound targeted to a CTGF nucleic acid results in a change in a measure of CTGF as measured by a standard test, for example, but not limited to, CTGF. In some embodiments, administration of a CTGF antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments pharmaceutical composition comprising an antisense compound targeted to CTGF is used for the preparation of a medicament for treating a patient suffering or susceptible to any one of the above-mentioned disorders.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include a second therapeutic agent. In certain such embodiments, pharmaceutical agents that may be co-administered with a pharmaceutical composition of the present invention include, but are not limited to second therapeutic agent. In certain such embodiments, the second therapeutic agent is administered prior to administration of a pharmaceutical composition of the present invention. In certain such embodiments, the second therapeutic agent is administered following administration of a pharmaceutical composition of the present invention. In certain such embodiments the second therapeutic agent is administered at the same time as a pharmaceutical composition of the present invention. In certain such embodiments the dose of a co-administered second therapeutic agent is the same as the dose that would be administered if the second therapeutic agent was administered alone. In certain such embodiments the dose of a co-administered second therapeutic agent is lower than the dose that would be administered if the second therapeutic agent was administered alone. In certain such embodiments the dose of a co-administered second therapeutic agent is greater than the dose that would be administered if the second therapeutic agent was administered alone.

In certain embodiments, the co-administration of a second compound enhances the therapeutic effect of a first compound, such that co-administration of the compounds results in a therapeutic effect that is greater than the effect of administering the first compound alone, a synergistic effect. In other embodiments, the co-administration results in therapeutic effects that are additive of the effects of the compounds when administered alone. In other embodiments, the co-administration results in therapeutic effects that are supra-additive of the effects of the compounds when administered alone. In some embodiments, the first compound is an antisense compound. In some embodiments, the second compound is an antisense compound.

This invention is illustrated in the Examples Section which follows. This section is set forth to aid in an understanding of the invention but is not intended to, and should not be construed to limit in any way the invention as set forth in the claims which follow thereafter.

EXAMPLES

Example 1

Selection of Lead Human Connective Tissue Growth Factors (CTGF) Antisense Oligonucleotides Candidate Introduction A series of oligonucleotides were designed to target different regions of the human connective tissue growth factor RNA, using published sequences (GenBank accession number NM_001901.2, incorporated herein as SEQ ID NO: 9, and GenBank accession number NT_025741.14, incorporated herein as SEQ ID NO: 10).

This study analyzes available sequence space and modified antisense oligonucleotides targeting both exonic and intronic space of CTGF. Approximately 150 novel sequences per target were synthesized and evaluated for activity against CTGF in cell-culture. The oligonucleotides are shown in Table 1. All compounds in Table 1 are chimeric oligonucleotides ("gapmers") 20 nucleotides in length, composed of a central "gap" region consisting of either ten 2'-deoxynucleotides, which is flanked on both sides (5' and 3' directions) by five-nucleotides "wings" or 13 2'-deoxynucleotides, which is flanked on both sides (5' and 3' directions) by two- and five-nucleotides "wings," respectively. The wings are composed of 2'-methoxyethyl (2'-MOE) nucleotides. The internucleoside (backbone) linkages are phosphorothioate (P=S) throughout the oligonucleotide. All cystidine residuals are 5-methycytidines. The compounds were analyzed for their effect on human connective tissue growth factor mRNA levels by quantitative real-time PCR as described later. Data are averages from two experiments. If present, "N.D." indicates "no data".

TABLE 1

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 124173 | CDS | 9 | 380 | CCAGCTGCTTGGCGCAGACG | 35 | 11 |
| 124189 | CDS | 9 | 1003 | GCCAGAAAGCTCAAACTTGA | 57 | 12 |
| 124212 | 3'-UTR | 9 | 1783 | CCACAAGCTGTCCAGTCTAA | 47 | 13 |
| 124235 | 3'-UTR | 9 | 2267 | GGTCACACTCTCAACAAATA | 47 | 14 |
| 124238 | 3'-UTR | 9 | 2282 | AAACATGTAACTTTTGGTCA | 53 | 15 |
| 412271 | 5'-UTR | 9 | 4 | GGGAAGAGTTGTTGTGTGAG | 0 | 16 |
| 412272 | 5'-UTR | 9 | 38 | AGGGTGGAGTCGCACTGGCT | 46 | 17 |
| 412273 | CDS | 9 | 228 | ACGAAGGCGACGCGGACGGG | 35 | 18 |
| 412274 | CDS | 9 | 265 | GCCGACGGCCGGCCGGCTGC | 40 | 19 |
| 412275 | CDS | 9 | 475 | GGTGCACACGCCGATCTTGC | 52 | 20 |
| 412276 | CDS | 9 | 483 | TCTTTGGCGGTGCACACGCC | 0 | 21 |
| 412277 | CDS | 9 | 489 | GCACCATCTTTGGCGGTGCA | 0 | 22 |
| 412278 | CDS | 9 | 496 | GCAGGGAGCACCATCTTTGG | 16 | 23 |
| 412279 | CDS | 9 | 501 | AAGATGCAGGGAGCACCATC | 63 | 24 |
| 412280 | CDS | 9 | 507 | CCACCGAAGATGCAGGGAGC | 0 | 25 |
| 412281 | CDS | 9 | 512 | CCGTACCACCGAAGATGCAG | 47 | 26 |
| 412282 | CDS | 9 | 553 | GTACTTGCAGCTGCTCTGGA | 68 | 27 |
| 412283 | CDS | 9 | 592 | GGGCATGCAGCCCACCGCCC | 72 | 28 |
| 412284 | CDS | 9 | 718 | AGGCCCAACCACGGTTTGGT | 59 | 29 |
| 412285 | CDS | 9 | 723 | AGGGCAGGCCCAACCACGGT | 79 | 30 |
| 412286 | CDS | 9 | 732 | TAAGCCGCGAGGGCAGGCCC | 55 | 31 |
| 412287 | CDS | 9 | 829 | CCCACAGGTCTTGGAACAGG | 30 | 32 |
| 412288 | CDS | 9 | 839 | AGATGCCCATCCCACAGGTC | 55 | 33 |
| 412289 | 3'-UTR | 9 | 1273 | CCAGTCTAATGAGTTAATGT | 56 | 34 |
| 412290 | 3'-UTR | 9 | 1281 | TTCAAGTTCCAGTCTAATGA | 10 | 35 |

TABLE 1-continued

Inhibition of human connective tissue growth factor mRNA levels by chimeric phosphorothioate oligo-nucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412291 | 3'-UTR | 9 | 1361 | TTTTCCCCCAGTTAGAAAAA | 38 | 36 |
| 412292 | 3'-UTR | 9 | 1388 | CACAATGTTTTGAATTGGGT | 50 | 37 |
| 412293 | 3'-UTR | 9 | 1394 | ACATGGCACAATGTTTTGAA | 67 | 38 |
| 412294 | 3'-UTR | 9 | 1399 | GTTTGACATGGCACAATGTT | 73 | 39 |
| 412295 | 3'-UTR | 9 | 1404 | TATTTGTTTGACATGGCACA | 74 | 40 |
| 412296 | 3'-UTR | 9 | 1412 | TGATAGACTATTTGTTTGAC | 35 | 41 |
| 412297 | 3'-UTR | 9 | 1457 | GTTCCACTGTCAAGTCTTAA | 55 | 42 |
| 412298 | 3'-UTR | 9 | 1469 | TGTACTAATGTAGTTCCACT | 69 | 43 |
| 412299 | 3'-UTR | 9 | 1482 | CATTCTGGTGCTGTGTACTA | 86 | 44 |
| 412300 | 3'-UTR | 9 | 1489 | TAATATACATTCTGGTGCTG | 76 | 45 |
| 412301 | 3'-UTR | 9 | 1495 | ACACCTTAATATACATTCTG | 54 | 46 |
| 412302 | 3'-UTR | 9 | 1502 | TAAAGCCACACCTTAATATA | 54 | 47 |
| 412303 | 3'-UTR | 9 | 1520 | GTACCCTCCCACTGCTCCTA | 53 | 48 |
| 412304 | 3'-UTR | 9 | 1554 | AAGATGCTATCTGATGATAC | 52 | 49 |
| 412305 | 3'-UTR | 9 | 1559 | CGTATAAGATGCTATCTGAT | 69 | 50 |
| 412306 | 3'-UTR | 9 | 1577 | AATAGCAGGCATATTACTCG | 74 | 51 |
| 412307 | 3'-UTR | 9 | 1586 | TACACTTCAAATAGCAGGCA | 66 | 52 |
| 412308 | 3'-UTR | 9 | 1591 | TCAATTACACTTCAAATAGC | 50 | 53 |
| 412309 | 3'-UTR | 9 | 1659 | GGAGAATGCACATCCTAGCT | 66 | 54 |
| 412310 | 3'-UTR | 9 | 1665 | ATGGCTGGAGAATGCACATC | 60 | 55 |
| 412311 | 3'-UTR | 9 | 1670 | TCTTGATGGCTGGAGAATGC | 71 | 56 |
| 412312 | 3'-UTR | 9 | 1729 | GAATCAGAATGTCAGAGCTG | 37 | 57 |
| 412313 | 3'-UTR | 9 | 1946 | CATTGAAATATCAAAGCATT | 0 | 58 |
| 412314 | 3'-UTR | 9 | 1952 | GGCTAACATTGAAATATCAA | 25 | 59 |
| 412315 | 3'-UTR | 9 | 1958 | AATTGAGGCTAACATTGAAA | 1 | 60 |
| 412316 | 3'-UTR | 9 | 1965 | GTTCAGAAATTGAGGCTAAC | 65 | 61 |
| 412317 | 3'-UTR | 9 | 1971 | TATGGTGTTCAGAAATTGAG | 13 | 62 |
| 412318 | 3'-UTR | 9 | 1976 | CTACCTATGGTGTTCAGAAA | 61 | 63 |
| 412319 | 3'-UTR | 9 | 1982 | TACATTCTACCTATGGTGTT | 38 | 64 |
| 412320 | 3'-UTR | 9 | 1991 | GACAAGCTTTACATTCTACC | 24 | 65 |
| 412321 | 3'-UTR | 9 | 1996 | GATCAGACAAGCTTTACATT | 37 | 66 |
| 412322 | 3'-UTR | 9 | 2007 | ATGCTTTGAACGATCAGACA | 64 | 67 |
| 412323 | 3'-UTR | 9 | 2012 | ATTTCATGCTTTGAACGATC | 44 | 68 |
| 412324 | 3'-UTR | 9 | 2018 | GTATCCATTTCATGCTTTGA | 60 | 69 |
| 412325 | 3'-UTR | 9 | 2026 | CCATATAAGTATCCATTTCA | 48 | 70 |
| 412326 | 3'-UTR | 9 | 2032 | GAATTTCCATATAAGTATCC | 28 | 71 |

TABLE 1-continued

Inhibition of human connective tissue growth factor mRNA levels by chimeric phosphorothioate oligo-nucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412327 | 3'-UTR | 9 | 2040 | TCTGAGCAGAATTTCCATAT | 58 | 72 |
| 412328 | 3'-UTR | 9 | 2050 | TGTCATTCTATCTGAGCAGA | 61 | 73 |
| 412329 | 3'-UTR | 9 | 2060 | TTTGACGGACTGTCATTCTA | 47 | 74 |
| 412330 | 3'-UTR | 9 | 2070 | AACAATCTGTTTTGACGGAC | 48 | 75 |
| 412331 | 3'-UTR | 9 | 2088 | TGATGCCTCCCCTTTGCAAA | 53 | 76 |
| 412332 | 3'-UTR | 9 | 2100 | TGCCAAGGACACTGATGCCT | 68 | 77 |
| 412333 | 3'-UTR | 9 | 2105 | CAGCCTGCCAAGGACACTGA | 75 | 78 |
| 412334 | 3'-UTR | 9 | 2110 | GAAATCAGCCTGCCAAGGAC | 60 | 79 |
| 412335 | 3'-UTR | 9 | 2115 | ACCTAGAAATCAGCCTGCCA | 46 | 80 |
| 412336 | 3'-UTR | 9 | 2120 | TTCCTACCTAGAAATCAGCC | 51 | 81 |
| 412337 | 3'-UTR | 9 | 2128 | TACCACATTTCCTACCTAGA | 59 | 82 |
| 412338 | 3'-UTR | 9 | 2134 | TGAGGCTACCACATTTCCTA | 0 | 83 |
| 412339 | 3'-UTR | 9 | 2140 | TAAAAGTGAGGCTACCACAT | 48 | 84 |
| 412340 | 3'-UTR | 9 | 2213 | CAAATGCTTCCAGGTGAAAA | 49 | 85 |
| 412341 | 3'-UTR | 9 | 2219 | TAGAAACAAATGCTTCCAGG | 66 | 86 |
| 412342 | 3'-UTR | 9 | 2230 | TCATATCAAAGTAGAAACAA | 12 | 87 |
| 412343 | 3'-UTR | 9 | 2242 | TCCGAAAAACAGTCATATCA | 24 | 88 |
| 412368 | Intron 1 | 10 | 1308 | ACCCGGCTGCAGAGGGCGAG | 0 | 89 |
| 412369 | Intron 1 | 10 | 1313 | CGCTTACCCGGCTGCAGAGG | 0 | 90 |
| 412370 | Intron 1 | 10 | 1410 | GACAGGGCGGTCAGCGGCGC | 0 | 91 |
| 412371 | Intron 2 | 10 | 1730 | AGTCCGAGCGGTTTCTTTTT | 0 | 92 |
| 412372 | Intron 2 | 10 | 1735 | AACTCAGTCCGAGCGGTTTC | 19 | 93 |
| 412373 | Intron 2 | 10 | 1740 | AAAGAAACTCAGTCCGAGCG | 10 | 94 |
| 412374 | Intron 2 | 10 | 1745 | TGGAGAAAGAAACTCAGTCC | 45 | 95 |
| 412375 | Intron 2 | 10 | 1750 | GCAGCTGGAGAAAGAAACTC | 14 | 96 |
| 412376 | Intron 2 | 10 | 1755 | TGGCAGCAGCTGGAGAAAGA | 46 | 97 |
| 412377 | Intron 2 | 10 | 1887 | AGGGAGCACCATCTTTGGCT | 20 | 98 |
| 412378 | Intron 3 | 10 | 2125 | TCACCCGCGAGGGCAGGCCC | 33 | 99 |
| 412379 | Intron 3 | 10 | 2137 | GGAAGACTCGACTCACCCGC | 0 | 100 |
| 412380 | Intron 3 | 10 | 2142 | TTAGAGGAAGACTCGACTCA | 0 | 101 |
| 412381 | Intron 3 | 10 | 2150 | ACCCTGACTTAGAGGAAGAC | 47 | 102 |
| 412382 | Intron 3 | 10 | 2155 | TCACGACCCTGACTTAGAGG | 31 | 103 |
| 412383 | Intron 3 | 10 | 2160 | GAGAATCACGACCCTGACTT | 2 | 104 |
| 412384 | Intron 3 | 10 | 2165 | TGGGAGAGAATCACGACCCT | 31 | 105 |
| 412385 | Intron 3 | 10 | 2170 | CTCCCTGGGAGAGAATCACG | 0 | 106 |
| 412386 | Intron 3 | 10 | 2191 | GGTCGGCACAGTTAGGACTC | 53 | 107 |

TABLE 1-continued

Inhibition of human connective tissue growth factor mRNA levels by chimeric phosphorothioate oligo-nucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412387 | Intron 3 | 10 | 2196 | CGTTCGGTCGGCACAGTTAG | 30 | 108 |
| 412388 | Intron 3 | 10 | 2216 | CCTGGATAAGGTATTTCCCC | 0 | 109 |
| 412389 | Intron 3 | 10 | 2235 | ACAAACACCATGTAAAACGC | 11 | 110 |
| 412390 | Intron 3 | 10 | 2241 | GAGCACACAAACACCATGTA | 0 | 111 |
| 412391 | Intron 3 | 10 | 2251 | TGCGAGAGCAGAGCACACAA | 0 | 112 |
| 412392 | Intron 3 | 10 | 2256 | TAAGCTGCGAGAGCAGAGCA | 2 | 113 |
| 412393 | Intron 3 | 10 | 2261 | GTCGGTAAGCTGCGAGAGCA | 23 | 114 |
| 412394 | Intron 3 | 10 | 2266 | TTCCAGTCGGTAAGCTGCGA | 15 | 115 |
| 412395 | Intron 4 | 10 | 2472 | ACATGTACCTTAATGTTCTC | 0 | 116 |
| 412396 | Intron 4 | 10 | 2477 | GCAGAACATGTACCTTAATG | 0 | 117 |
| 412397 | Intron 4 | 10 | 2482 | TAGGAGCAGAACATGTACCT | 9 | 118 |
| 412398 | Intron 4 | 10 | 2487 | GTTAATAGGAGCAGAACATG | 19 | 119 |
| 412399 | Intron 4 | 10 | 2496 | TGAAAATAGTTAATAGGAG | 0 | 120 |
| 412400 | Intron 4 | 10 | 2511 | CCACTGTTTTTCCTGTGAAA | 10 | 121 |
| 412401 | Intron 4 | 10 | 2525 | AAGTTGGGTCCTATCCACTG | 28 | 122 |
| 412402 | Intron 4 | 10 | 2530 | GCCCTAAGTTGGGTCCTATC | 20 | 123 |
| 412403 | Intron 4 | 10 | 2535 | CAAGAGCCCTAAGTTGGGTC | 0 | 124 |
| 412404 | Intron 4 | 10 | 2540 | CGTGGCAAGAGCCCTAAGTT | 64 | 125 |
| 412405 | Intron 4 | 10 | 2558 | CGGGCTTATACTAACAAGCG | 6 | 126 |
| 412406 | Intron 4 | 10 | 2563 | GATAACGGGCTTATACTAAC | 33 | 127 |
| 412407 | Intron 4 | 10 | 2568 | TTGGAGATAACGGGCTTATA | 73 | 128 |
| 412408 | Intron 4 | 10 | 2573 | TAGTTTTGGAGATAACGGGC | 51 | 129 |
| 412409 | Intron 4 | 10 | 2578 | TTAGATAGTTTTGGAGATAA | 24 | 130 |
| 412410 | Intron 4 | 10 | 2584 | CAATGGTTAGATAGTTTTGG | 36 | 131 |
| 412411 | Intron 4 | 10 | 2589 | CAGCTCAATGGTTAGATAGT | 53 | 132 |
| 412412 | Intron 4 | 10 | 2594 | CAAAACAGCTCAATGGTTAG | 34 | 133 |
| 412413 | Intron 4 | 10 | 2599 | TCCAGCAAAACAGCTCAATG | 59 | 134 |
| 412414 | Intron 4 | 10 | 2604 | CTCATTCCAGCAAAACAGCT | 42 | 135 |
| 412415 | Intron 4 | 10 | 2609 | AAGCTCTCATTCCAGCAAAA | 57 | 136 |
| 412416 | Intron 4 | 10 | 2614 | TACACAAGCTCTCATTCCAG | 44 | 137 |
| 412417 | Intron 4 | 10 | 2623 | GGTTGCTATTACACAAGCTC | 72 | 138 |
| 412418 | Intron 4 | 10 | 2628 | CTGGTGGTTGCTATTACACA | 61 | 139 |
| 412419 | Intron 4 | 10 | 2633 | GAAAACTGGTGGTTGCTATT | 29 | 140 |
| 412420 | Intron 4 | 10 | 2638 | TAGTGGAAAACTGGTGGTTG | 5 | 141 |
| 412421 | Intron 4 | 10 | 2663 | TTAACTAACCCTGTGGAAGA | 15 | 142 |
| 412422 | Intron 4 | 10 | 2672 | TGTCTTGAATTAACTAACCC | 4 | 143 |

TABLE 1-continued

Inhibition of human connective tissue growth factor mRNA levels by chimeric phosphorothioate oligo-nucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412423 | Intron 4 | 10 | 2677 | TGGAATGTCTTGAATTAACT | 0 | 144 |
| 412424 | Intron 4 | 10 | 2691 | GCCAGAGCCTCTCTTGGAAT | 36 | 145 |
| 412425 | Intron 4 | 10 | 2698 | AAAAATAGCCAGAGCCTCTC | 59 | 146 |
| 412426 | Intron 4 | 10 | 2703 | TGTCCAAAAATAGCCAGAGC | 28 | 147 |
| 412427 | Intron 4 | 10 | 2708 | TGCTATGTCCAAAAATAGCC | 15 | 148 |
| 412428 | Intron 4 | 10 | 2713 | TCATTTGCTATGTCCAAAAA | 28 | 149 |
| 412429 | Intron 4 | 10 | 2718 | GAGTCTCATTTGCTATGTCC | 20 | 150 |
| 412430 | Intron 4 | 10 | 2723 | AGTTTGAGTCTCATTTGCTA | 30 | 151 |
| 412431 | Intron 4 | 10 | 2728 | GAGGAAGTTTGAGTCTCATT | 55 | 152 |
| 412432 | Intron 4 | 10 | 2763 | CTTCTGTTGTCTGACTTCTG | 55 | 153 |
| 412433 | Intron 4 | 10 | 2778 | CCTCTGTGTTTTAGTCTTCT | 56 | 154 |
| 412434 | Intron 4 | 10 | 2788 | TTTCTTCAACCCTCTGTGTT | 15 | 155 |
| 412435 | Intron 4 | 10 | 2796 | GGAGTGGCTTTCTTCAACCC | 43 | 156 |
| 412436 | Intron 4 | 10 | 2849 | AGGAAGACAAGGGAAAAGAG | 20 | 157 |
| 412437 | Intron 4 | 10 | 2854 | TTCTAAGGAAGACAAGGGAA | 0 | 158 |
| 412438 | Intron 4 | 10 | 2859 | TGCCCTTCTAAGGAAGACAA | 31 | 159 |
| 412439 | Intron 2 | 10 | 1791 | GGATGCGAGTTGGGATCTGG | 0 | 160 |
| 412440 | CDS | 9 | 380 | CCAGCTGCTTGGCGCAGACG | 64 | 161 |
| 412441 | CDS | 9 | 1003 | GCCAGAAAGCTCAAACTTGA | 37 | 162 |
| 412442 | 3'-UTR | 9 | 1783 | CCACAAGCTGTCCAGTCTAA | 32 | 163 |
| 412443 | 3'-UTR | 9 | 2267 | GGTCACACTCTCAACAAATA | 59 | 164 |
| 412444 | 3'-UTR | 9 | 2282 | AAACATGTAACTTTTGGTCA | 55 | 165 |
| 418899 | 3'-UTR | 9 | 1391 | TGACATGGCACAATGTTTTG | ND* | 166 |

*ND—i.e. not determined in the experiment but was highly active in another assay.

As shown in Table 1, SEQ ID NOs 11-15, 17-20, 24, 26-34, 36-57, 59, 61, 63-82, 84-86, 88, 95, 97, 99, 102, 103, 105, 107, 108, 122, 125, 127-140, 145, 146, 149, 151-154, 156, 159, 161-165 demonstrated at least 24% inhibition of human connective tissue growth factor expression in this assay and are therefore preferred. The target sites to which these preferred sequences are complementary are herein referred to as "active sites" and are therefore preferred sites for targeting by compounds of the present invention.

The antisense compound is complementary within a range of nucleotides on the CTGF sequence, i.e. within the range of nucleotides 718-751, 1388-1423, 1457-1689, 2040-2069, 2120-2147, or 2267-2301 of SEQ ID NO: 9. In a certain embodiment the antisense compound is complementary within the range of nucleotides 2728-2797 of SEQ ID NO: 10. Compounds targeted to these ranges demonstrate at least 50% inhibition (i.e. SEQ ID NOs: 15, 29, 31, 42, 46-49, 53, 72, 81, 82, 152-154, 164, and 165). Certain target sites listed in Table 1 also demonstrate at least 50% inhibition (i.e. SEQ ID NOs: 12, 20, 33, 34, 76, 107, 129, 132, 134, 136, and 146).

In certain embodiments the antisense compound is complementary within the range of nucleotides 553-611, 1394-1423, 1469-1508, 1559-1605, 1659-1689 or 2100-2129. Compounds targeted therein demonstrate at least 60% inhibition (i.e. SEQ ID NOs: 27, 38, 43, 50, 52, 54, 55, 77, 79, and 86). Certain target sites listed in Table 1 also demonstrate at least 60% inhibition (i.e. SEQ ID NOs: 24, 61, 63, 67, 69, 73, 125, 139 and 161).

The antisense compound is also complementary within the range of nucleotides 1399-1423. Compounds targeted therein demonstrate at least 70% inhibition (i.e. SEQ ID NOs: 39 and 40). Certain target sites listed in Table 1 also demonstrate at least 70% inhibition (i.e. SEQ ID NOs: 28, 30, 45, 51, 56, 78, 128, and 138). One target site listed in Table 1 also demonstrates at least 80% inhibition (i.e. SEQ ID NO: 44). In certain embodiments, the percent inhibition is achieved when the antisense compound is delivered to HuVec cells at a concentration of 50 nm.

Multiple leads with apparent activity greater than the historical ASO lead sequence, SEQ ID No. 15 (ISIS 124238), were identified in both exonic and intronic sequences.

Materials and Methods

Oligonucleotides were evaluated and activity confirmed at a concentration 50 nM in human umbilical vein endothelial cells (HuVEC) using Lipofectin mediated transfection. HuVEC cells from Cascade Biologics (Portland, Oreg.) maintained in Medium 200 supplemented with Low Serum Growth Supplement (from Cascade Biologics) were plated into 96-well plates at 5,000 cells per well and incubated overnight at 37° C. in the presence of 5% $CO_2$. The following day the medium was aspirated and replaced with prewarmed Opti-MEM I (Invitrogen) containing Oligo-Lipofectamine 2000 (Invitrogen) mixture (3 mg of Lipofectamine 2000 per 1 ml of Opti-MEM I medium). After 4 hours, the transfection mixture was exchanged for fresh Medium 200 supplemented with Low Serum Growth Supplement and incubated at 37° C. in the presence of 5% $CO_2$. After 16-24 hours, at approximately 80% confluence, the cells were washed with phosphate buffer saline (PBS) and lysed for RNA purification with the Qiagen RNeasy Kit. CTGF message was measured by quantitative real time polymerase chain reaction (RT-PCR) (Primer/Probe sets shown below) and the results were normalized to total RNA.

Statistical Analysis

Each sample was analyzed in duplicate, and vertical bars represent the spread between the two measurements.

Results and Discussion

Of the approximately 150 novel sequences per target synthesized and evaluated for activity against CTGF in cell-culture, the CTGF oligonucleotides (SEQ ID NOs: 28, 30, 39, 40, 45, 52, 56, 78, 125, and 166) show excellent inhibition of human CTGF mRNA expression.

Example 2

A Single-Dose Intra-Dermal Pharmacokinetic Study of CTGF Antisense Oligonucleotide in Rabbits Study Objective The purpose of this pharmacokinetic study in rabbit is to evaluate the diffusion and concentration of a CTGF antisense oligonucleotide (SEQ ID NO:39, ISIS 412294) in rabbit skin at different times subsequent to a single intra-dermal injection.

Study Design

On day 0 of the study all animals were dosed intra-dermally (ID) with a single 100 μL injection of CTGF antisense oligonucleotide SEQ ID NO:39 at a concentration of 50 mg/mL (5 mg total dose). The animals were dosed with the antisense oligonucleotide in a site to the left of the spinal mid-line, roughly parallel to the rabbit's shoulders and adjacent to a suture 3 cm incisional wound (FIG. 1A). The needle was inserted so that the test material was injected down towards the base of the animal's body. On days 1, 3, 7 or 14, the rabbits were euthanized and two full-thickness 1.0 cm punch biopsies were obtained, one centered over the original injection site and the other vertically below spaced 0.5 cm apart. The samples were snap frozen and stored at −80° C. prior to analysis of the antisense oligonucleotide drug levels using a hybridization capture method. Results represent the mean antisense oligonucleotide levels from both biopsies at the indicated time.

Results and Conclusions

Figure 1B:
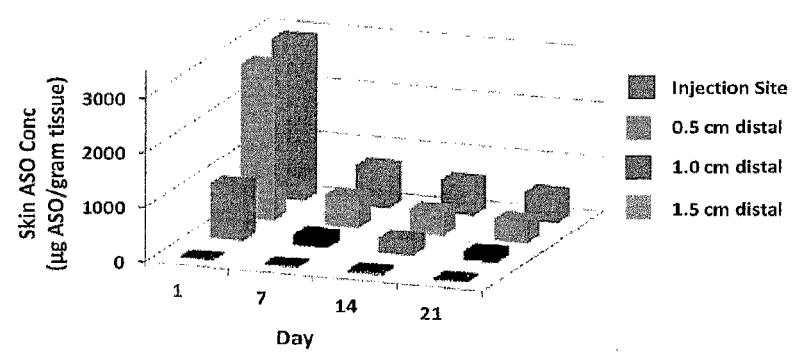

Significant levels of the antisense oligonucleotide are present up to 14 days after intradermal dosing (see FIG. 1B). The antisense oligonucleotide also remains close to the original site of injection (≤1 cm), with very limited lateral diffusion distal to the site of administration (FIG. 1B). For example, levels of ASO are very low at distances 1.5 cm distal to the injection site at all times post injection. Therefore the pharmacological effects of this class of molecule will be limited to areas of skin immediately adjacent to the injection site. To overcome this limitation, an intradermal injection threading technique has been developed (and used in clinical studies) which delivers equal amounts of antisense along the full length of the developing scar. These results demonstrate two novel findings. First, that there is a prolonged residence time of a 2'MOE antisense oligonucleotide with this chemical configuration in skin; and second, antisense oligonucleotides have very limited lateral diffusion in skin. The latter limitation of this class of molecule can be overcome by dosing the antisense oligonucleotide by a threading technique as described previously.

Example 3

Animal Study with CTGF Antisense Oligonucleotide Targeting Human Keloids in an In Vivo Model System Study Objective The purpose of this study was to evaluate the efficacy of antisense oligonucleotides targeting human CTGF in an in vivo model system using a human keloid/mouse xenograft model. The oligonucleotide tested was antisense oligonucleotide No. 412300 (SEQ ID NO: 45).

Methods

Human Keloid/Mouse Xenograft Model.

A human keloid/mouse xenograft model using transplanted human keloid tissue into nude mice was used.

Fresh specimens of keloid tissue were obtained anonymously, from discarded tissue of patients undergoing elective excision of keloids for cosmetic reasons. The keloid samples were processed into 10×5×5 mm samples and weighed on an analytical balance. The keloid samples were then implanted into the mice as described below.

Mice were anaesthetized using 3% isoflurane. Buprenorphine was given before surgery and post-operatively, as needed (Buprenorphine at 0.3 mg/ml; 2 mg/kg; SC).

After achieving general anesthesia and prepping the animal, two 10 mm incisions were made in the skin, over the left and right scapula, and a pouch created using fine-tipped scissors, between subcutaneous fat and the fascia. One keloid sample was inserted into each pouch. The incisions were closed with veterinary grade cyanoacrylate glue (VetBond or Nexaband) and the area swabbed with 70% ethanol. The area was then dressed with sterile semi-permeable membranes (Op-Site™, Smith and Nephew).

Evaluation of ASOs In Vivo Against Keloids

An ASO targeting human (and not mouse) CTGF was used (antisense oligonucleotide No. 412300; SEQ ID NO: 45). To test the efficacy of the ASO in the in vivo model system described above, keloid implants were injected with either ASO (dissolved in PBS) or PBS control. There were two groups of animals with 8 animals per group (with two keloids/animal). Animals were allowed to acclimate for approximately 2 weeks post keloids implantation prior to ASO dosing.

A total dose of 500 μg of oligo per keloid sample was administered in a total volume of 100 μl (from a stock solution of 5.0 mg/ml). The ASO or PBS control was administered immediately adjacent to each implant for a total of 4 weeks, twice a week. One week after the last injection, one implant was removed and subjected to qRT-PCR for gene expression analysis, and the contralateral keloid removed and analyzed histology for the collagen content using integrated density of fluorescence (IDF).

Total RNA was isolated and either CTGF or collagen, type III, alpha 1 (Col3A1) mRNA determined by quantitative real-time PCR using primer pairs that have been shown to be specific for human mRNA sequences. The mRNA levels were correlated with the GAPDH levels in the same samples, and any changes in the ASO-treated samples over the control treated by PBS alone were calculated.

Results

Figure 2A:
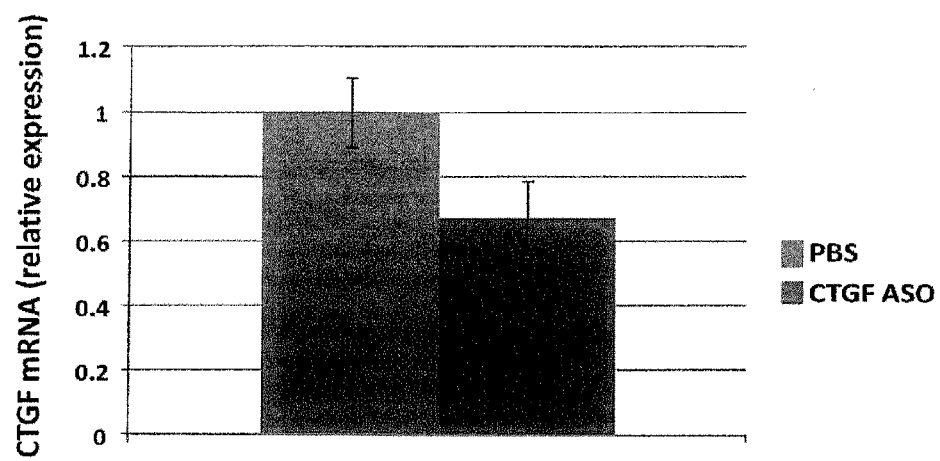
FIG. 2 shows that treatment of keloids in an animal model, with a CTGF antisense oligonucleotide resulted in reduction in both CTGF (FIG. 2A) and Col3a1 (FIG. 2B) mRNA expression in intact human keloid tissue transplanted into mice (described in Example 3).
Figure 2B:
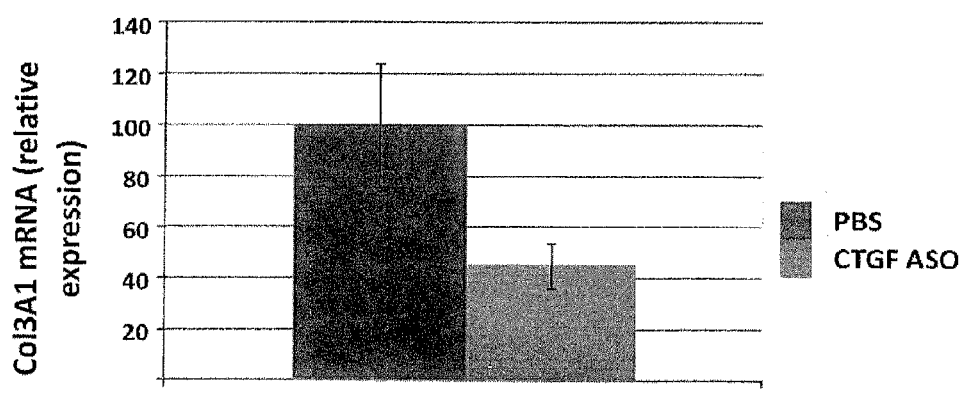

Results following 4 weeks of treatment with 500 µg of antisense oligonucleotide No. 412300 (SEQ ID NO: 45) in a total volume of 100 µl per keloid sample indicates reduction in CTGF and Col3A1 mRNA expression in individual keloid samples. Treatment with the CTGF ASO reduced CTGF mRNA expression in the keloid tissue to 67% control (p=0.082) (FIG. 2A). Treatment with the CTGF ASO reduced Col3a1 mRNA expression in the keloid tissue to 45% control (p=0.153) (FIG. 2B).

Conclusion

Keloids are characterized by abnormal proliferation of fibroblasts and overproduction of different forms of collagen. Histo-pathologically, they are characterized by the presence of whorls and nodules of thick, hyalinized collagen bundles or keloidal collagen with mucinous ground substance and relatively few fibroblasts in the dermis of keloid scars. The large thick collagen bundles and numerous thin fibrils are closely packed together. Type III collagen is the second most abundant collagen found in the skin, and is very abundant in keloids. Col3A1 is significantly elevated in keloids compared to normal skin.

It has been demonstrated here for the first time, the ability of 2'MOE chemically modified ASOs to reduce CTGF in intact, human keloid tissue. Treatment of the human keloid tissues with an ASO CTGF reduced the target CTGF mRNA expression by 33%. This has also resulted in a reduction in Col3A1 expression of 55%. This reduction in Col3A1 expression would lead to a significant therapeutic benefit in patients suffering from keloid growth, and demonstrate the utility of a 2'MOE ASO as a novel drug for the treatment of keloids.

Example 4

Breast Scar Revision Study in Humans

Study Objective

This is a randomized, double-blind, within-subject controlled clinical study evaluating efficacy and safety of a CTGF antisense oligonucleotides (EXC 001) in subjects undergoing elective revision of scars resulting from prior breast surgery. This study requires that the subjects to have pre-existing scars of sufficient severity to warrant scar revision surgery. Thus, this study pre-screen for subjects who could be expected to have a high rate of hypertrophic scar or keloids formation in the revised placebo-treated scars.

In patients who have had prior surgery of the breast and now have bilateral matching scars at the same anatomic locations, EXC 001 (SEQ ID NO:39) or placebo was administered to the portion of the revised breast scars via intradermal threading injections. The primary objective of the study was to assess the efficacy of EXC 001 in reducing subsequent skin scarring. The secondary objective of the study was to assess the safety of EXC 001.

Methods

A 6 cm section of either side of the revised breast wound/scar was treated with 4 doses of EXC 001 or placebo, at 2, 5, 8, and 11 weeks after the surgical incision was closed. Randomization determined which side was treated with EXC 001 or placebo in each subject.

Dosage of EXC 001 used was 5 mg per linear centimeter. Concentration of EXC 001 used was 25 mg/ml and 100 ul of EXC 001 was injected per linear centimeter of the revised breast wound/scar. Injections were made on both sides of each incision, with half of the amount per linear centimeter administered on each side. The injections on a given side were 3 cm apart. In order to deliver placebo or EXC 001 adjacent to and along the length of the incision, intradermal needles (3 cm long) were used for injections. The needle is inserted immediately adjacent to the surgical incision on each side by a threading technique, and EXC 001 or placebo is injected as needle is withdrawn, so that equal amounts of antisense drug are administered along the length of the scar.

The study duration was approximately 31 weeks. The subjects receive the scar revisions on Day 1, followed by 4 doses of EXC 001 and placebo, at 2, 5, 8, and 11 weeks after the surgical incisions were closed. Scar observation and assessment were performed at week 24.

Efficacy was determined by rating each matched pair of incisions from individual patients (within subject analysis). Efficacy was evaluated at week 24 following scar revision surgery, using three methods of rating severity of incisional scars:

Subject assessment of their scars. On a scale of 1-10 the patient rated their "overall" opinion on the appearance of the scar.

Physician (investigator) assessment of the scars. On a scale of 1-10 the physician rated overall opinion of scar appearance.

Expert Panel assessment of pairs of blinded scar photographs, using a 100 mm Visual Analog Scale (VAS), where 0=best possible scar and 100=worst possible scar. This method gives information on the absolute severity of the scars as well as the differences between the two scars in the pair.

Results 21 subjects completed this study. Examination of the week 24 post-surgery photographs indicate that nearly all of the subjects show recurrence of hypertrophic scars on at least one side following scar revision surgery. In some cases, the scars extend beyond the boundaries of the original incisions and are therefore keloidal scars.

This study achieved statistically significant results in favor of EXC 001 in all three endpoints (a negative score represents the difference between placebo and EXC 001 treated, in favor of EXC 001—see Table 2 below).

The subject assessment of their scars:

The "overall" rating was statistically significant in favor of EXC 001 (p=0.033).

The physician assessment of the scars:
   The "overall" rating was highly statistically significant in favor of EXC 001 (p<0.001).
   Expert panel VAS rating of photographs was also highly statistically significant in favor of EXC 001 (p<0.001).

TABLE 2

| Scar Assessmant Scale | Difference between placebo and EXC 001 | p-value |
|---|---|---|
| Subject Overall | −2.4 | 0.003 |
| Physician Overall | −2.3 | <0.001 |
| Expert VAS | −26.0 | <0.001 |

FIG. 3A shows that treatment with the CTGF antisense oligonucleotide, (EXC 001 or SEQ ID NO: 39), inhibits formation and growth of a hypertrophic scar at 24 weeks post surgery. FIG. 3B shows results from a different subject, also at 24 weeks. In this second example, the patient has developed a keloid at 24 weeks post revision surgery in the placebo treated scar. In contrast, the formation and growth of a keloid scar at the adjacent scar revision site was almost completely prevented by treatment with EXC 001.

Therefore, in these two examples, the growth of both hypertrophic scars and keloid scars are inhibited by treatment with EXC 001. The scores below each set of pictures represent the degree of improvement between placebo- and EXC 001-treated scars. For example, an expert VAS score of −19.3 indicates that the placebo scar is worse than the corresponding EXC 001-treated scar by 19.3 on a 100 point scale. The physician and subject scores of −1 means that the placebo-treated scar is worse than the corresponding EXC 001-treated scar by 1 point on a 10 point scale. The result demonstrates that EXC 001 reduces the severity of both hypertrophic scars and keloid scars.

Example 5

Primary Prevention Abdominoplasty Study in Humans

Study Objective
   This is a randomized, double-blind, within-subject controlled clinical study evaluating efficacy and safety of a CTGF antisense oligonucleotides (EXC 001) in subjects undergoing elective abdominoplast surgery.
Method
   Study duration was 24 weeks. Subjects received the abdominoplasty on day 1, followed by treatment with either EXC 001 or placebo over a 9 week period.
   Dosage of EXC 001 used was 5 mg per linear centimeter. Concentration of EXC 001 used was 25 mg/ml and 100 ul of EXC 001 was injected per linear centimeter of the abdominoplasty wound/scar. Injections were made on both sides of each incision, with half of the amount per linear centimeter administered on each side. Either drug or placebo was dosed along two 6 cm portions of the scar at each lateral end of the scar, and so the dosed sections are separated by at least 10 cm untreated scar. The injections on a given side were 3 cm apart. In order to deliver placebo or EXC 001 adjacent to and along the length of the incision, intradermal needles (3 cm long) were used for injections. The needle is inserted immediately adjacent to the surgical incision on each side using a threading technique, and EXC 001 or placebo is injected as needle is withdrawn.
   The subjects receive the scar revisions on Day 1, followed by 4 doses of EXC 001 and placebo, at 2, 5, 8, and 11 weeks after the surgical incisions were closed. Scar observation and assessment were performed at week 12.
   Efficacy is determined by rating each matched portion of the dosed incision (placebo treated compared to EXC 001 treated) using the three methods of rating scar severity of incisional scars as described in the previous example.
Results
   EXC 001 is efficacious by these criteria at week 12. An example of the efficacy is shown in FIG. 4. In this example, the reduction in scar severity resulting from EXC 001 dosing compared to placebo dosing is clearly seen. The placebo treated section of the incision has developed into a hypertrophic scar whereas the EXC 001 treated section of the scar is more fine-line.
   Another example of the ability of EXC 001 to reduce the formation of hypertrophic scars is shown in FIG. 5. In this example, the section of the abdominoplasty on the right side of the scar (to the right of the vertical line) was treated with EXC 001 whereas the scar to the left of the vertical line did not receive any treatment. Clearly the scar severity to the right is less severe than to the left.
   This example also demonstrates that the EXC 001 therapeutic benefit is limited to the region of scar directly adjacent to the site of drug intradermal threading dosing. Therefore the drug appears to have limited diffusion away from the sire of administration and will require dosing immediately adjacent to the scar, for example by intradermal threading.

Example 6

Biomarker Study Demonstrating Effect of EEC 001 on mRNA Expression of Various Genes in Humans Method
   13 weeks prior to an abdominoplasty procedure, an area between the umbilicus and the suprapubic hairline was used as a site to create a total of twenty 2 cm incisions. The 2 cm long incisions were in four columns of four incisions (A, B, C, D) and were used for RNA analysis at week 13 post-incisions. Two additional incisions lateral to these columns on each side of the abdomen (a, b, and c, d) were used for 4 or 8 weeks post-incisions mRNA analysis. Each column was separated by at least 4 cm and each incision separated by at least 3 cm.
   Treatments of incisional wounds with either EXC 001 or placebo were randomly assigned to two treatment groups. All four incisional wounds in each of the columns A, B, C, and D received the same EXC 001 or placebo dose. All the incisional wounds/scars on one side of the abdomen received injections of EXC 001 and the other side received injections of placebo. All injections were blinded to the individual receiving the test agents. All incisions/scars in a given subject were treated on the same dosage schedule.
   Thirty subjects were randomly assigned to one of three cohorts of 10 subjects each; each cohort was treated on a different dosage schedule (but the high and low doses were the same for all cohorts):
Cohort #1: Intradermal injections at weeks 2, 4, 6, 8, and 10
Cohort #2: Intradermal injections at weeks 2, 5, 8, and 11
Cohort #3: Intradermal injections at weeks 2, 6, and 10
   A 27 gauge needle, approximately 38 mm long, was inserted intradermally 2 cm (the entire length of each incision), parallel to and approximately 3 mm from the incisional wound/scar (intradermal threading technique). Either EXC 001 or placebo was then injected while gradually withdrawing the needle so that the correct amount per linear centimeter was evenly deposited into the dermis along the incision line.

Biopsy of Incisions

One 6 mm punch biopsy on each side adjacent to the lateral incisions were taken at day 1 for mRNA analysis and used as control for unwounded skin samples. At week 4, the 9 patients in cohort 1, and at week 8, the 20 patients in cohorts 2 and 3 were biopsied from their lateral incisions (a, b, c, d). Two of these incisions received EXC 001, and two received placebo through randomized assignment. Just prior to the abdominoplasty surgery (at week 13), each of the scars in columns A, B, C, and D were scored for scar severity (by Physician and Expert Panel Scales, see Example 5 above), and also sampled for both histological and RNA analysis.

Results

There was a statistically significant improvement observed for EXC 001 treated vs placebo treated scars for the Physician Overall Opinion when all cohorts were combined at the high dose level (8.7%, p-value=0.018). There was also a statistically significant mean difference observed for the Overall evaluation of all cohorts combined and all doses combined (5.9%, p-value=0.016). These results again demonstrate the ability of EXC 001 to reduce scar severity.

Figure 6:
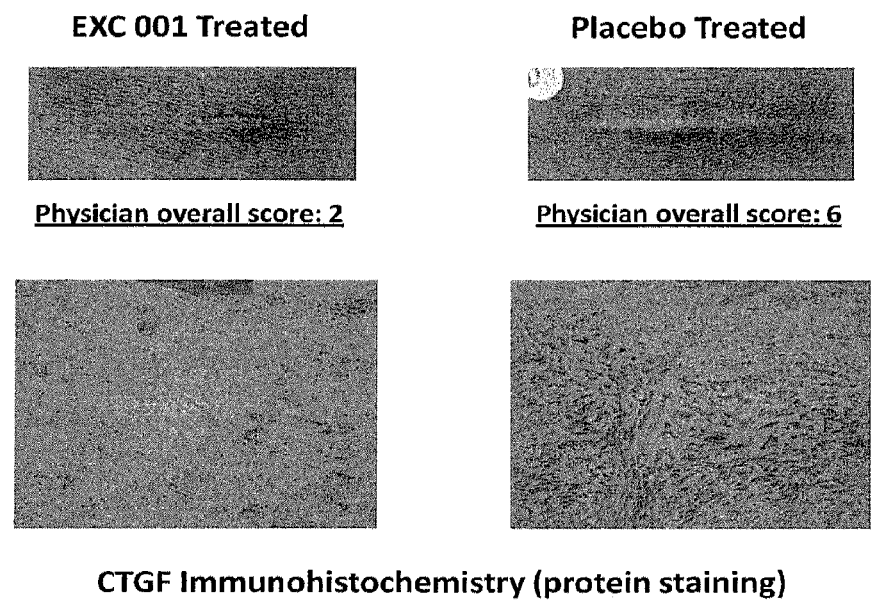
FIG. 6 shows an example of the ability of EXC 001 to reduce the growth and formation of hypertrophic scars (described in Example 6). In this example, two matching 2 cm abdominal scars are shown, one treated with 5 mg/cm EXC 001 and one with placebo. The severity of the EXC 001 treated scar is less than the placebo treated scar. Histological analysis of these two scars also revealed an EXC 001 mediated reduction in the expression of CTGF protein (by immunohistochemistry) clearly demonstrating that EXC 001 is functioning to reduce the expression of its intended target (CTGF).

An example of the ability of EXC 001 to reduce the growth and formation of hypertrophic scars is shown in FIG. 6. In this example, two matching scars are shown, one treated with 5 mg/cm EXC 001 and one with placebo. The severity of the EXC 001 treated scar is less than the placebo treated scar.

Histological analysis of these two scars also revealed an EXC 001 mediated reduction in the expression of CTGF protein (by immunohistochemistry) clearly demonstrating that EXC 001 is functioning to reduce the expression of its intended target (CTGF). Analysis of expression of 9 different mRNA transcripts was also performed at 4, 8, and 13 weeks post wounding (Table 3)

TABLE 3

| mRNA transcripts analyzed by XP-PCR | |
|---|---|
| Gene Measured | Identifier (Accession) |
| Collagen1-a1 (COL1A1) | NM_000088 |
| Collagen1-a2 (COL1A2) | NM_000089 |
| Collagen III-a1 (COL3A1) | NM_000090 |
| Connective Tissue Growth Factor (CTGF) | NM_001901 |
| Transforming Growth factor-beta1 (TGF-β1) | NM_000660 |

TABLE 3-continued

| mRNA transcripts analyzed by XP-PCR | |
|---|---|
| Gene Measured | Identifier (Accession) |
| Mothers Against Decapentaplegic Homolog 3 (SMAD3) | NM_005902 |
| Elastin | M_36860 |
| Matrix metalloproteinase 1 (MMP-1) | NM_002421 |
| α-smooth muscle actin (α-SMA/ACTA2) | NM_001613 |

Following post-surgical wounding, increased mRNA expression of CTGF and collagen genes were anticipated. CTGF mRNA expression in the scars was increased from baseline unwounded skin at all three times points, and in all three cohorts (approximately 2-5 fold). Increased expression of a variety of genes known to be associated with scarring, including the collagen genes, such as Col1A2 (5-8 fold) and Col3A1 (3-7 fold), was also observed, as would be expected in developing scar tissues.

Figure 7A:
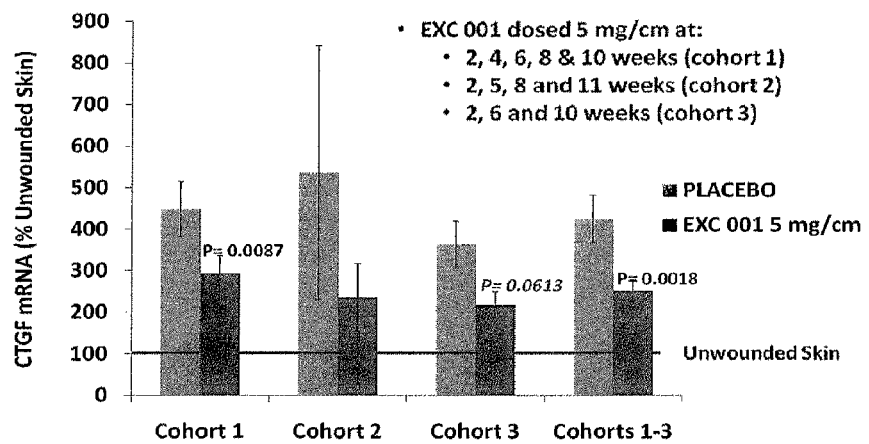
FIG. 7A shows the effect of EXC 001 in suppressing CTGF mRNA expression.
Figure 7B:
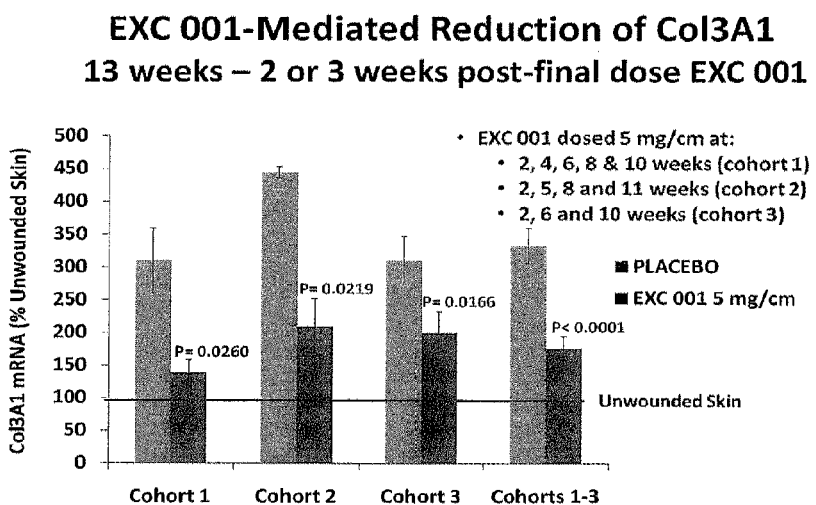
FIG. 7B shows the effect of EXC 001 in suppressing Collagen III-a1 (Col3A1) mRNA expression.
Figure 7C:
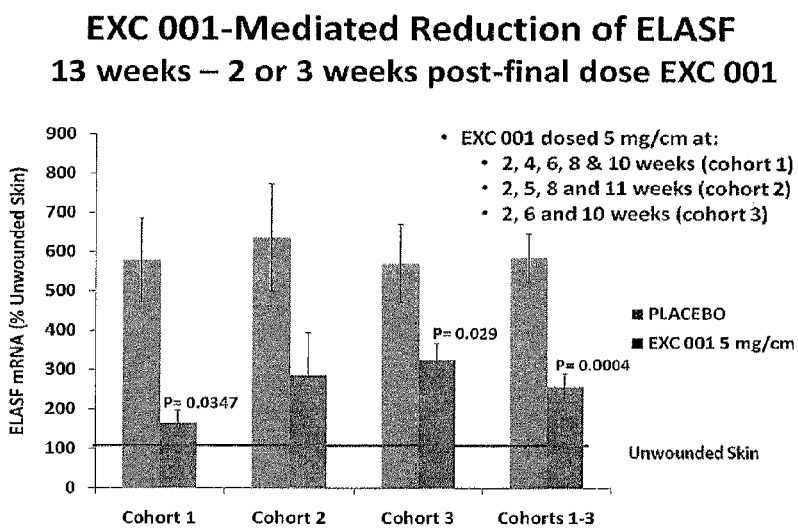
FIG. 7C shows the effect of EXC 001 in suppressing elastin (ELASF) mRNA expression.
Figure 7D:
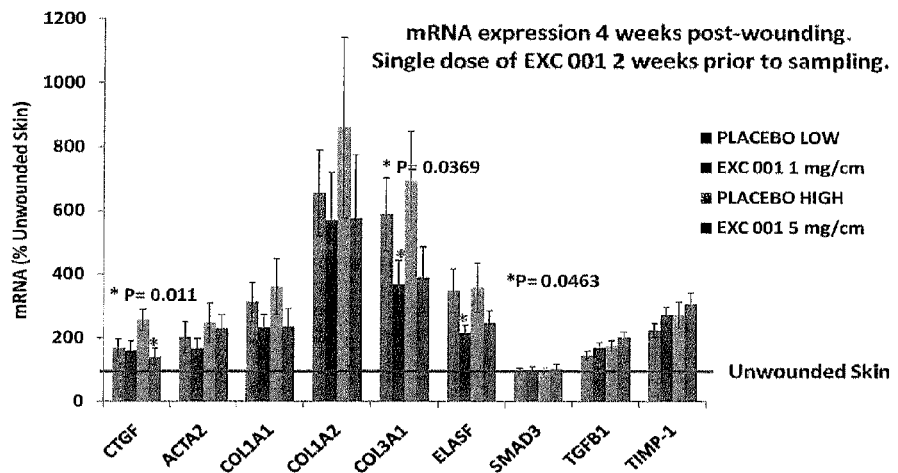
FIGS. 7D and E shows there was no significant inhibition of either SMAD3 or TGF-β1 mRNA expression by EXC 001 as compared to placebo.
Figure 7E:
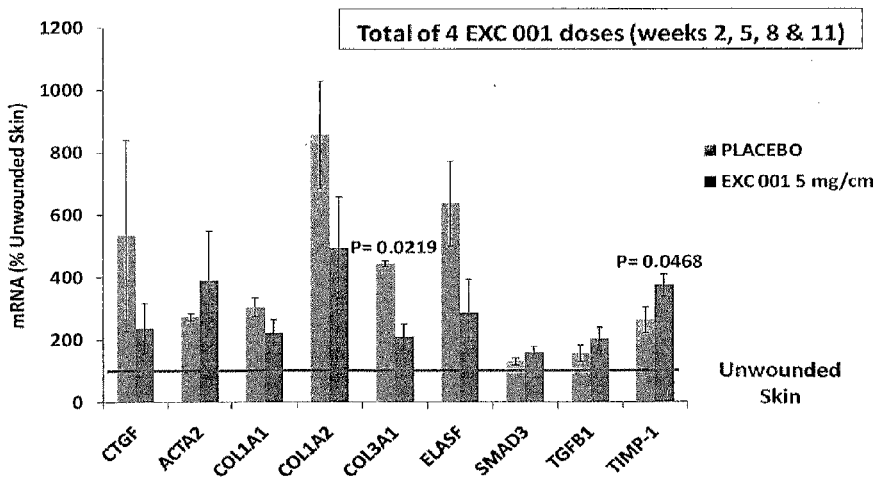
FIG. 7 shows the effects of EXC 001 on mRNA expression in abdominal scars of various genes at various timespost treatment (described in Example 6).

When compared to the corresponding placebo treated scar at all three time-points measured, suppression of CTGF mRNA induction was observed following EXC 001 injections. As shown in FIG. 7A, at week 13, the overall (across all 3 cohorts) EXC 001 mediated reduction in CTGF mRNA induction was 53%. The degree of CTGF mRNA suppression also varied with time and cohort dosing. For example, in one cohort a single dose of 5 mg/cm reduced the induction in expression of CTGF by 74% (p=0.011) to an induction of only 140% expression compared to unwounded skin (measurement taken two weeks after the last dose of EXC 001) (FIG. 7D). In addition, the overall induced mRNA expression levels of Col1A2, Col3A1 (FIG. 7B), and elastin fibers (ELASF) (FIG. 7C) were also significantly decreased (by 40% (p=0.0013), 69% (p<0.0001), and 63% (p=0.0004), respectively) by EXC 001 treatment, when measured at week 13 (across all three cohorts).

Complete inhibition of collagen gene expression would likely not be a desirable outcome of drug treatment, as some collagen gene expression is required to facilitate normal wound repair and healing processes. As shown in FIGS. 7D and E, there was no significant inhibition of either SMAD3 or TGFβ1 mRNA expression by EXC 001 treatment compared to placebo at weeks 4 or 13.

These data demonstrate a mechanism of action for EXC 001 in human. These data also demonstrate a mechanism by which EXC 001 is able to reduce the severity of skin scarring.

What is claimed is:

1. A method for treating a keloid, or preventing the formation, reformation, or growth of a keloid after an injury to the skin, in a subject in need thereof, which comprises administering to the subject by one or more injections at the site of the keloid or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the keloid, wherein the effective amount is from 0.1 to 50 mg of the modified oligonucleotide per injection per linear centimeter of the keloid or of the injury to the skin.

2. A method for treating a hypertrophic scar, or preventing the formation, reformation, or growth of a hypertrophic scar after an injury to the skin, in a subject in need thereof, which comprises administering to the subject by one or more injections at the site of the hypertrophic scar or of the injury to the skin, a composition which comprises a modified oligonucleotide consisting of 12-30 linked nucleosides, at least a 12 nucleobase sequence portion of which is present within a region selected from nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129 and 1399-1423 of SEQ ID NO: 9, or a salt or ester thereof, in an amount effective to treat, or to prevent the formation, reformation, or growth of, the hypertrophic scar, wherein the effective amount is from 0.1 to 25 mg of the modified oligonucleotide per injection per linear centimeter of the hypertrophic scar or of the injury to the skin.

3. A method for reducing formation, reformation, or growth of a scar or keloid at a site of an injury to the skin, or of treating a pre-existing scar or keloid, in a subject in need thereof, which comprises administering to the subject by one or more threading injections at the site of the injury or of the pre-existing scar or keloid, a composition which comprises a modified oligonucleotide, or a salt or ester thereof, targeted to a nucleic acid encoding a protein involved in fibrosis in an amount effective to inhibit expression of the protein and thereby reduce scar or keloid formation, reformation, or growth at the site of the injury or to treat the pre-existing scar or keloid.

4. The method of claim 3, wherein the one or more threading injections comprise multiple intradermal threading injections per scar.

5. A method for reducing formation, reformation, or growth of a fibrotic lesion at a site of an injury, or of treating a pre-existing fibrotic lesion, in a subject in need thereof, which comprises administering to the subject by one or more threading injections at the site of the injury or of the pre-existing fibrotic lesion, a composition which comprises a modified oligonucleotide, or a salt or ester thereof, targeted to a nucleic acid encoding a protein involved in fibrosis in an amount effective to inhibit expression of the protein and thereby reduce formation, reformation, or growth of the fibrotic lesion at the site of the injury or to treat the preexisting fibrotic lesion.

6. The method of claim 3, wherein the protein involved in fibrosis is connective tissue growth factor.

7. The method of claim 3, wherein the effective amount is from 0.1 to 25 mg of the modified oligonucleotide per injection per linear centimeter of the site of the injury to the skin or of the pre-existing scar.

8. The method of claim 3, wherein the modified oligonucleotide is administered at least once every two weeks for at least four weeks, at least once every three weeks for at least six weeks, at least once every four weeks for at least eight weeks, at least once every eight weeks for at least sixteen weeks, over a period of at least nine weeks, or over a period of 26 weeks.

9. The method of claim 6, wherein the modified oligonucleotide consists of 12-30 linked nucleosides, at least a 12 nucleobase sequence portion of which is present within a region selected from the group consisting of nucleotides 553-611, 718-751, 1388-1423, 1457-1689, 2040-2069, 2120-2147, 2728-2797, 2267-2301, 1394-1423, 1469-1508, 1559-1605, 1659-1689, 2100-2129, and 1399-1423 of SEQ ID NO: 9.

10. The method of claim 6, wherein at least a 12 nucleobase sequence portion of the modified oligonucleotide is present within the nucleobase sequence set forth in any of the sequences set forth in SEQ ID NO: 28, 30, 39, 40, 43, 44, 45, 50, 51, 52, 56, 78, 125, or 166.

11. The method of claim 10, wherein the modified oligonucleotide is a single-stranded or a double-stranded oligonucleotide.

12. The method of claim 10, wherein the modified oligonucleotide comprises at least one oligodeoxyribonucleotide or at least one oligoribonucleotide.

13. The method of claim 10, wherein the modified oligonucleotide has a sequence which is 100% identical over its length to a portion of any one of the sequences set forth in SEQ ID NO: 28, 30, 39, 40, 43, 44, 45, 50, 51, 52, 56, 78, 125, or 166.

14. The method of claim 13, wherein the modified oligonucleotide comprises at least one modified internucleoside linkage.

15. The method of claim 13, wherein at least one nucleoside comprises a modified sugar.

16. The method of claim 13, wherein at least one nucleoside comprises a modified nucleobase.

17. The method of claim 13, wherein the modified oligonucleotide comprises:
(a) a gap segment consisting of linked deoxynucleosides;
(b) a 5' wing segment consisting of linked modified nucleosides; and
(c) a 3' wing segment consisting of linked modified nucleosides;
wherein the gap segment is positioned between the 5' wing segment and the 3' wing segment and wherein each modified nucleoside within each wing segment comprises a modified sugar.

18. The method of claim 17, wherein the modified oligonucleotide comprises:
(a) a gap segment consisting of thirteen linked deoxynucleosides;
(b) a 5' wing segment consisting of two linked modified nucleosides; and
(c) a 3' wing segment consisting of five linked modified nucleosides;
wherein the gap segment is positioned between the 5' wing segment and the 3' wing segment, wherein each modified nucleoside within each wing segment comprises a 2'-O-methoxyethyl sugar; and wherein each internucleoside linkage is a phosphothioate linkage.

19. The method of claim 10, wherein the sequence of the nucleobase is the sequence set forth in SEQ ID NO:39.

20. The method of claim 3, further comprises comprising administering to the subject a second compound.

21. The method of claim 3, wherein the modified oligonucleotide is present in a conjugate with a moiety which enhances uptake of the compound into, and/or increases residence time of the compound in, the subject, wherein the residence time is 7 to 60 days or in a delivery system which enhances uptake of the compound into, and/or increases residence time of the compound in, the subject, wherein the residence time is 7 to 60 days.

22. The method of claim 3, wherein the injury to the skin is the result of a surgical incision, a biopsy, a skin piercing, a skin removal, a burn, or a wound.

23. The method of claim 3, wherein the effective amount is about 5 mg of the modified oligonucleotide per injection per linear centimeter of the keloid, the injury to the skin, the site of the injury, or the pre-existing scar.

24. The method of claim 3, wherein the modified oligonucleotide is administered by means of a formulation, ultrasound, electroporation, iontophoresis or micro-needle.

25. The method of claim 3, wherein the modified oligonucleotide is administered adjacent to the keloid, the injury to the skin, the site of the injury, or the pre-existing scar; along the entire length of the keloid, the injury to the skin, the site of the injury, or the pre-existing scar; along each side of the keloid, the injury to the skin, the site of the injury, or the pre-existing scar; or directly into the keloid, the injury to the skin, the site of the injury, or the pre-existing scar.

26. The method of claim 3, wherein the modified oligonucleotide is administered intradermally, sub-cutaneously, or topically.

27. The method of claim 3, wherein the modified oligonucleotide is administered intradermally by threading technique.

* * * * *

SEQUENCE LISTING

<160> NUMBER OF SEQ ID NOS: 167

<210> SEQ ID NO 1
<211> LENGTH: 20
<212> TYPE: DNA
<213> ORGANISM: Artificial Sequence
<220> FEATURE:
<223> OTHER INFORMATION: Positive control oligonucleotide directed to
      human H-ras

<400> SEQUENCE: 1
tccgtcatcg ctcctcaggg                                              20

<210> SEQ ID NO 2
<211> LENGTH: 2075
<212> TYPE: DNA
<213> ORGANISM: Homo sapiens
<220> FEATURE:
<221> NAME/KEY: exon

<222> LOCATION: (130)..(1180)

<400> SEQUENCE: 2

```
cccggccgac agccccgaga cgacagcccg gcgcgtcccg gtccccacct ccgaccaccg      60
ccagcgctcc aggccccgcg ctccccgctc gccgccaccg cgccctccgc tccgcccgca     120 gtgccaacc atg acc gcc gcc agt atg ggc ccc gtc cgc gtc gcc ttc gtg    171
           Met Thr Ala Ala Ser Met Gly Pro Val Arg Val Ala Phe Val
             1               5                  10 gtc ctc ctc gcc ctc tgc agc cgg ccg gcc gtc ggc cag aac tgc agc      219
Val Leu Leu Ala Leu Cys Ser Arg Pro Ala Val Gly Gln Asn Cys Ser
 15              20                  25                  30 ggg ccg tgc cgg tgc ccg gac gag ccg gcg ccg cgc tgc ccg gcg ggc      267
Gly Pro Cys Arg Cys Pro Asp Glu Pro Ala Pro Arg Cys Pro Ala Gly
                 35                  40                  45 gtg agc ctc gtg ctg gac ggc tgc ggc tgc tgc cgc gtc tgc gcc aag      315
Val Ser Leu Val Leu Asp Gly Cys Gly Cys Cys Arg Val Cys Ala Lys
         50                  55                  60 cag ctg ggc gag ctg tgc acc gag cgc gac ccc tgc gac ccg cac aag      363
Gln Leu Gly Glu Leu Cys Thr Glu Arg Asp Pro Cys Asp Pro His Lys
     65                  70                  75 ggc ctc ttc tgt gac ttc ggc tcc ccg gcc aac cgc aag atc ggc gtg      411
Gly Leu Phe Cys Asp Phe Gly Ser Pro Ala Asn Arg Lys Ile Gly Val
 80                  85                  90 tgc acc gcc aaa gat ggt gct ccc tgc atc ttc ggt ggt acg gtg tac      459
Cys Thr Ala Lys Asp Gly Ala Pro Cys Ile Phe Gly Gly Thr Val Tyr
 95                 100                 105                 110 cgc agc gga gag tcc ttc cag agc agc tgc aag tac cag tgc acg tgc      507
Arg Ser Gly Glu Ser Phe Gln Ser Ser Cys Lys Tyr Gln Cys Thr Cys
                115                 120                 125 ctg gac ggg gcg gtg ggc tgc atg ccc ctg tgc agc atg gac gtt cgt      555
Leu Asp Gly Ala Val Gly Cys Met Pro Leu Cys Ser Met Asp Val Arg
            130                 135                 140 ctg ccc agc cct gac tgc ccc ttc ccg agg agg gtc aag ctg ccc ggg      603
Leu Pro Ser Pro Asp Cys Pro Phe Pro Arg Arg Val Lys Leu Pro Gly
        145                 150                 155 aaa tgc tgc gag gag tgg gtg tgt gac gag ccc aag gac caa acc gtg      651
Lys Cys Cys Glu Glu Trp Val Cys Asp Glu Pro Lys Asp Gln Thr Val
160                 165                 170 gtt ggg cct gcc ctc gcg gct tac cga ctg gaa gac acg ttt ggc cca      699
Val Gly Pro Ala Leu Ala Ala Tyr Arg Leu Glu Asp Thr Phe Gly Pro
175                 180                 185                 190 gac cca act atg att aga gcc aac tgc ctg gtc cag acc aca gag tgg      747
Asp Pro Thr Met Ile Arg Ala Asn Cys Leu Val Gln Thr Thr Glu Trp
                195                 200                 205 agc gcc tgt tcc aag acc tgt ggg atg ggc atc tcc acc cgg gtt acc      795
Ser Ala Cys Ser Lys Thr Cys Gly Met Gly Ile Ser Thr Arg Val Thr
            210                 215                 220 aat gac aac gcc tcc tgc agg cta gag aag cag agc cgc ctg tgc atg      843
Asn Asp Asn Ala Ser Cys Arg Leu Glu Lys Gln Ser Arg Leu Cys Met
        225                 230                 235 gtc agg cct tgc gaa gct gac ctg gaa gag aac att aag aag ggc aaa      891
Val Arg Pro Cys Glu Ala Asp Leu Glu Glu Asn Ile Lys Lys Gly Lys
240                 245                 250 aag tgc atc cgt act ccc aaa atc tcc aag cct atc aag ttt gag ctt      939
Lys Cys Ile Arg Thr Pro Lys Ile Ser Lys Pro Ile Lys Phe Glu Leu
255                 260                 265                 270 tct ggc tgc acc agc atg aag aca tac cga gct aaa ttc tgt gga gta      987
Ser Gly Cys Thr Ser Met Lys Thr Tyr Arg Ala Lys Phe Cys Gly Val
                275                 280                 285
```

```
tgt acc gac ggc cga tgc tgc acc ccc cac aga acc acc acc ctg ccg      1035
Cys Thr Asp Gly Arg Cys Cys Thr Pro His Arg Thr Thr Thr Leu Pro
            290                 295                 300 gtg gag ttc aag tgc cct gac ggc gag gtc atg aag aag aac atg atg      1083
Val Glu Phe Lys Cys Pro Asp Gly Glu Val Met Lys Lys Asn Met Met
        305                 310                 315 ttc atc aag acc tgt gcc tgc cat tac aac tgt ccc gga gac aat gac      1131
Phe Ile Lys Thr Cys Ala Cys His Tyr Asn Cys Pro Gly Asp Asn Asp
    320                 325                 330 atc ttt gaa tcg ctg tac tac agg aag atg tac gga gac atg gca tga a   1180
Ile Phe Glu Ser Leu Tyr Tyr Arg Lys Met Tyr Gly Asp Met Ala
335                 340                 345 gccagagagt gagagacatt aactcattag actggaactt gaactgattc acatctcatt    1240
tttccgtaaa aatgatttca gtagcacaag ttatttaaat ctgttttctc aactggggga    1300
aaagattccc acccaattca aaacattgtg ccatgtcaaa caaatagtct atcttcccca    1360
gacactggtt tgaagaatgt taagacttga cagtggaact acattagtac acagcaccag    1420
aatgtatatt aaggtgtggc tttaggagca gtgggagggt accggcccgg ttagtatcat    1480
cagatcgact cttatacgag taatatgcct gctatttgaa gtgtaattga aaggaaaat     1540 tttagcgtgc tcactgacct gcctgtagcc ccagtgacag ctaggatgtg cattctccag    1600
ccatcaagag actgagtcaa gttgttcctt aagtcagaac agcagactca gctctgacat    1660
tctgattcga atgacactgt tcaggaatcg gaatcctgtc gattagactg gacagcttgt    1720
ggcaagtgaa tttgcctgta caagccaga tttttttaaaa tttatattgt aaatattgtg    1780
tgtgtgtgtg tgtgtgtata tatatatata tatgtacagt tatctaagtt aatttaaagt    1840
tgtttgtgcc tttttatttt tgtttttaat gctttgatat ttcaatgtta gcctcaattt    1900
ctgaacacca taggtagaat gtaaagcttg tctgatcgtt caaagcatga aatggatact    1960
tatatgaaaa ttctgctcag atagaatgac agtccgtcaa aacagattgt ttgcaaaggg    2020
gaggcatcag tgtcttggca ggctgatttc taggtaggaa atgtggtagc tcacg         2075

<210> SEQ ID NO 3
<211> LENGTH: 22
<212> TYPE: DNA
<213> ORGANISM: Artificial Sequence
<220> FEATURE:
<223> OTHER INFORMATION: Forward PCR primer directed to human connective
      tissue growth factor (CTGF)

<400> SEQUENCE: 3
acaagggcct cttctgtgac tt                                              22

<210> SEQ ID NO 4
<211> LENGTH: 22
<212> TYPE: DNA
<213> ORGANISM: Artificial Sequence
<220> FEATURE:
<223> OTHER INFORMATION: Reverse PCR primer directed to human connective
      tissue growth factor (CTGF)

<400> SEQUENCE: 4
ggtacaccgt accaccgaag at                                              22

<210> SEQ ID NO 5
<211> LENGTH: 23
<212> TYPE: DNA
<213> ORGANISM: Artificial Sequence
<220> FEATURE:
```

<223> OTHER INFORMATION: PCR probe directed to human connective tissue
      growth factor (CTGF)

<400> SEQUENCE: 5
tgtgcaccgc caaagatggt gct                                             23

<210> SEQ ID NO 6
<211> LENGTH: 19
<212> TYPE: DNA
<213> ORGANISM: Artificial Sequence
<220> FEATURE:
<223> OTHER INFORMATION: Forward PCR primer directed to human GAPDH

<400> SEQUENCE: 6
gaaggtgaag gtcggagtc                                                  19

<210> SEQ ID NO 7
<211> LENGTH: 20
<212> TYPE: DNA
<213> ORGANISM: Artificial Sequence
<220> FEATURE:
<223> OTHER INFORMATION: Reverse PCR primer directed to human GAPDH

<400> SEQUENCE: 7
gaagatggtg atgggatttc                                                 20

<210> SEQ ID NO 8
<211> LENGTH: 20
<212> TYPE: DNA
<213> ORGANISM: Artificial Sequence
<220> FEATURE:
<223> OTHER INFORMATION: PCR probe directed to human GAPDH

<400> SEQUENCE: 8
caagcttccc gttctcagcc                                                 20

<210> SEQ ID NO 9
<211> LENGTH: 2358
<212> TYPE: DNA
<213> ORGANISM: Homo sapiens
<220> FEATURE:
<221> NAME/KEY: exon
<222> LOCATION: (207)..(1256)

<400> SEQUENCE: 9
aaactcacac aacaactctt ccccgctgag aggagacagc cagtgcgact ccaccctcca     60
gctcgacggc agccgccccg gccgacagcc ccgagacgac agcccggcgc gtccggtcc     120 ccacctccga ccaccgccag cgctccaggc cccgccgctc ccgctcgcc gccaccgcgc     180 cctccgctcc gcccgcagtg ccaacc atg acc gcc gcc agt atg ggc ccc gtc     233
                              Met Thr Ala Ala Ser Met Gly Pro Val
                               1               5 cgc gtc gcc ttc gtg gtc ctc ctc gcc ctc tgc agc cgg ccg gcc gtc     281
Arg Val Ala Phe Val Val Leu Leu Ala Leu Cys Ser Arg Pro Ala Val
 10                  15                  20                  25 ggc cag aac tgc agc ggg ccg tgc cgg tgc ccg gac gag ccg gcg ccg     329
Gly Gln Asn Cys Ser Gly Pro Cys Arg Cys Pro Asp Glu Pro Ala Pro
                 30                  35                  40 cgc tgc ccg gcg ggc gtg agc ctc gtg ctg gac ggc tgc ggc tgc tgc     377
Arg Cys Pro Ala Gly Val Ser Leu Val Leu Asp Gly Cys Gly Cys Cys
             45                  50                  55 cgc gtc tgc gcc aag cag ctg ggc gag ctg tgc acc gag cgc gac ccc     425
Arg Val Cys Ala Lys Gln Leu Gly Glu Leu Cys Thr Glu Arg Asp Pro
         60                  65                  70

```
tgc gac ccg cac aag ggc ctc ttc tgt gac ttc ggc tcc ccg gcc aac      473
Cys Asp Pro His Lys Gly Leu Phe Cys Asp Phe Gly Ser Pro Ala Asn
 75                  80                  85 cgc aag atc ggc gtg tgc acc gcc aaa gat ggt gct ccc tgc atc ttc      521
Arg Lys Ile Gly Val Cys Thr Ala Lys Asp Gly Ala Pro Cys Ile Phe
 90                  95                 100                 105 ggt ggt acg gtg tac cgc agc gga gag tcc ttc cag agc agc tgc aag      569
Gly Gly Thr Val Tyr Arg Ser Gly Glu Ser Phe Gln Ser Ser Cys Lys
                    110                 115                 120 tac cag tgc acg tgc ctg gac ggg gcg gtg ggc tgc atg ccc ctg tgc      617
Tyr Gln Cys Thr Cys Leu Asp Gly Ala Val Gly Cys Met Pro Leu Cys
            125                 130                 135 agc atg gac gtt cgt ctg ccc agc cct gac tgc ccc ttc ccg agg agg      665
Ser Met Asp Val Arg Leu Pro Ser Pro Asp Cys Pro Phe Pro Arg Arg
        140                 145                 150 gtc aag ctg ccc ggg aaa tgc tgc gag gag tgg gtg tgt gac gag ccc      713
Val Lys Leu Pro Gly Lys Cys Cys Glu Glu Trp Val Cys Asp Glu Pro
    155                 160                 165 aag gac caa acc gtg gtt ggg cct gcc ctc gcg gct tac cga ctg gaa      761
Lys Asp Gln Thr Val Val Gly Pro Ala Leu Ala Ala Tyr Arg Leu Glu
170                 175                 180                 185 gac acg ttt ggc cca gac cca act atg att aga gcc aac tgc ctg gtc      809
Asp Thr Phe Gly Pro Asp Pro Thr Met Ile Arg Ala Asn Cys Leu Val
                190                 195                 200 cag acc aca gag tgg agc gcc tgt tcc aag acc tgt ggg atg ggc atc      857
Gln Thr Thr Glu Trp Ser Ala Cys Ser Lys Thr Cys Gly Met Gly Ile
            205                 210                 215 tcc acc cgg gtt acc aat gac aac gcc tcc tgc agg cta gag aag cag      905
Ser Thr Arg Val Thr Asn Asp Asn Ala Ser Cys Arg Leu Glu Lys Gln
        220                 225                 230 agc cgc ctg tgc atg gtc agg cct tgc gaa gct gac ctg gaa gag aac      953
Ser Arg Leu Cys Met Val Arg Pro Cys Glu Ala Asp Leu Glu Glu Asn
    235                 240                 245 att aag aag ggc aaa aag tgc atc cgt act ccc aaa atc tcc aag cct     1001
Ile Lys Lys Gly Lys Lys Cys Ile Arg Thr Pro Lys Ile Ser Lys Pro
250                 255                 260                 265 atc aag ttt gag ctt tct ggc tgc acc agc atg aag aca tac cga gct     1049
Ile Lys Phe Glu Leu Ser Gly Cys Thr Ser Met Lys Thr Tyr Arg Ala
                270                 275                 280 aaa ttc tgt gga gta tgt acc gac ggc cga tgc tgc acc ccc cac aga     1097
Lys Phe Cys Gly Val Cys Thr Asp Gly Arg Cys Cys Thr Pro His Arg
            285                 290                 295 acc acc acc ctg ccg gtg gag ttc aag tgc cct gac ggc gag gtc atg     1145
Thr Thr Thr Leu Pro Val Glu Phe Lys Cys Pro Asp Gly Glu Val Met
        300                 305                 310 aag aag aac atg atg ttc atc aag acc tgt gcc tgc cat tac aac tgt     1193
Lys Lys Asn Met Met Phe Ile Lys Thr Cys Ala Cys His Tyr Asn Cys
    315                 320                 325 ccc gga gac aat gac atc ttt gaa tcg ctg tac tac agg aag atg tac     1241
Pro Gly Asp Asn Asp Ile Phe Glu Ser Leu Tyr Tyr Arg Lys Met Tyr
330                 335                 340                 345 gga gac atg gca tga agccagagag tgagagacat taactcatta gactggaact     1296
Gly Asp Met Ala tgaactgatt cacatctcat ttttccgtaa aaatgatttc agtagcacaa gttatttaaa    1356 tctgttttc taactgggggg aaaagattcc cacccaattc aaaacattgt gccatgtcaa    1416
acaaatagtc tatcaacccc agacactggt ttgaagaatg ttaagacttg acagtggaac    1476
tacattagta cacagcacca gaatgtatat taaggtgtgg ctttaggagc agtgggaggg    1536
```

-continued

```
taccagcaga aaggttagta tcatcagata gcatcttata cgagtaatat gcctgctatt   1596
tgaagtgtaa ttgagaagga aaattttagc gtgctcactg acctgcctgt agccccagtg   1656
acagctagga tgtgcattct ccagccatca agagactgag tcaagttgtt ccttaagtca   1716
gaacagcaga ctcagctctg acattctgat tcgaatgaca ctgttcagga tcggaatcc    1776 tgtcgattag actggacagc ttgtggcaag tgaatttgcc tgtaacaagc cagatttttt   1836
aaaatttata ttgtaaatat tgtgtgtgtg tgtgtgtgtg tatatatata tatatgtaca   1896
gttatctaag ttaatttaaa gttgtttgtg ccttttttatt tttgtttttta atgctttgat  1956 atttcaatgt tagcctcaat ttctgaacac cataggtaga atgtaaagct tgtctgatcg   2016
ttcaaagcat gaaatggata cttatatgga aattctgctc agatagaatg acagtccgtc   2076
aaaacagatt gtttgcaaag gggaggcatc agtgtccttg gcaggctgat ttctaggtag   2136
gaaatgtggt agcctcactt ttaatgaaca aatggccttt attaaaaact gagtgactct   2196
atatagctga tcagttttttt cacctggaag catttgtttc tactttgata tgactgtttt   2256
tcggacagtt tatttgttga gagtgtgacc aaaagttaca tgtttgcacc tttctagttg    2316
aaaataaagt gtatatttttt tctataaaaa aaaaaaaaa aa                        2358
```

<210> SEQ ID NO 10
<211> LENGTH: 6001
<212> TYPE: DNA
<213> ORGANISM: Homo sapiens

<400> SEQUENCE: 10

```
tatattattc actgtcaatc ttagtttata tccagataca acagggtaca ctgctcttgt     60
aatggaatca gacttcttat tttaacaaga caaaccaaat ccaatccaca tttgaagatt    120
ataggtttta atataagaaa atgcactcat ttctcaaaga ccctagtgaa gctgtgttta   180
aatgctccta ggtgaacccc ctttgcatcc cagtgttccc accctgacac ccagagcccc   240
tacctaccca acacagaatc atttgctctg atagaacaat ggatcccttt ttctggaaac   300
attgatggcc actcctccct tgtccttgcc tatataaaac tcctacatat attaagagaa   360
aactaagcaa gagttttgga aatctgcccc aggagactgc atcctgagtc acacgcgtct   420
ttgttctctt tcttgtccca aaaccgttac ctcaagtgac aaatgatcaa atctcaaata   480
tagaattcag ggttttacag gtaggcatct tgaggatttc aaatggttaa aagcaactca   540
ctccttttct actctttgga gagtttcaag agcctatagc ctctaaaacg caaatcattg   600
ctaagggttg ggggggagaa accttttcga attttttagg aattcctgct gtttgcctct   660
tcagctacct acttcctaaa aaggatgtat gtcagtggac agaacagggc aaacttattc   720
gaaaaagaaa taagaaataa ttgccagtgt gtttataaat gatatgaatc aggagtggtg   780
cgaagaggat agggaaaaaa aaattctatt tggtgctgga aatactgcgc ttttttttttt  840 ccttttttttt tttttctgtg agctggagtg tgccagcttt ttcagacgga ggaatgctga   900
gtgtcaaggg gtcaggatca atccggtgtg agttgatgag gcaggaaggt ggggaggaat   960
gcgaggaatg tccctgtttg tgtaggactc cattcagctc attggcgagc gcggccgcc   1020 cggagcgtat aaaagcctcg ggccgccgc cccaaactca cacaacaact cttccccgct   1080
gagaggagac agccagtgcg actccaccct ccagctcgac ggcagccgcc ccggccgaca   1140
gccccgagac gacagcccgg cgcgtccggg tccccacctc cgaccaccgc cagcgctcca   1200
ggccccgccg ctcccgctc gccgccaccg cgccctccgc tccgcccgca gtgccaacca   1260
```

```
tgaccgccgc cagtatgggc cccgtccgcg tcgccttcgt ggtcctcctc gccctctgca    1320
gccgggtaag cgccgggagc ccccgctgcg gccggcggct gccagggagg gactcggggc    1380
cggccgggga gggcgtgcgc gccgaccgag cgccgctgac cgccctgtcc tccctgcagc    1440
cggccgtcgg ccagaactgc agcgggccgt gccggtgccc ggacgagccg cgccgcgct    1500
gcccggcggg cgtgagcctc gtgctggacg gctgcggctg ctgccgcgtc tgcgccaagc    1560
agctgggcga gctgtgcacc gagcgcgacc catgcgaccc gcacaagggc ctattctgtc    1620
acttcggctc cccggccaac cgcaagatcg gcgtgtgcac cggtaagacc cgcagccccc    1680
accgctaggt gtccggccgc ctcctccctc acgcccaccc gcccgctgga aaagaaacc    1740
gctcggactg agtttctttc tccagctgct gccagcccgc ccctgcagc ccagatccca    1800
actcgcatcc ctgacgctct ggatgtgaga gtgccccaat gcctgacctc tgcatccccc    1860
acccctctct tcccttcctc ttctccagcc aaagatggtg ctccctgcat cttcggtggt    1920
acggtgtacc gcagcggaga gtccttccag agcagctgca agtaccagtg cacgtgcctg    1980
gacggggcgg tgggctgcat gccctgtgc agcatggacg ttcgtctgcc cagccctgac    2040
tgccccttcc cgaggagggt caagctgccc gggaaatgct gcgaggagtg ggtgtgtgac    2100
gagcccaagg accaaaccgt ggttgggcct gccctcgcgg gtgagtcgag tcttcctcta    2160
agtcagggtc gtgattctct cccagggagg gagtcctaac tgtgccgacc gaacggggga    2220
aataccttat ccaggcgttt tacatggtgt ttgtgtgctc tgctctcgca gcttaccgac    2280
tggaagacac gtttggccca gacccaacta tgattagagc caactgcctg gtccagacca    2340
cagagtggag cgcctgttcc aagacctgtg ggatgggcat ctccacccgg ttaccaatg    2400
acaacgcctc ctgcaggcta gagaagcaga gccgcctgtg catggtcagg ccttgcgaag    2460
ctgacctgga agagaacatt aaggtacatg ttctgctcct attaactatt tttcacagga    2520
aaaacagtgg ataggaccca acttagggct cttgccacgc ttgttagtat aagcccgtta    2580
tctccaaaac tatctaacca ttgagctgtt ttgctggaat gagagcttgt gtaatagcaa    2640
ccaccagttt tccactacga aatcttccac agggttagtt aattcaagac attccaagag    2700
aggctctggc tatttttgga catagcaaat gagactcaaa cttcctcccc tcaaaatata    2760
aacagaagtc agacaacaga agactaaaac acagagggtt gaagaaagcc actcctcttg    2820
tagagtcgct gatttttttt ttcctctct cttttccctt gtcttcctta gaagggcaaa    2880
aagtgcatcc gtactcccaa aatctccaag cctatcaagt ttgagctttc tggctgcacc    2940
agcatgaaga cataccgagc taaattctgt ggagtatgta ccgacggccg atgctgcacc    3000
ccccacagaa ccaccaccct gccggtggag ttcaagtgcc ctgacggcga ggtcatgaag    3060
aagaacatga tgttcatcaa gacctgtgcc tgccattaca actgtcccgg agacaatgac    3120
atctttgaat cgctgtacta caggaagatg tacggagaca tggcatgaag ccagagagtg    3180
agagacatta actcattaga ctggaacttg aactgattca catctcattt ttccgtaaaa    3240
atgatttcag tagcacaagt tatttaaatc tgttttcta actgggggaa aagattccca    3300
cccaattcaa acattgtgc catgtcaaac aaatagtcta tcaaccccag acactggttt    3360
gaagaatgtt aagacttgac agtggaacta cattagtaca cagcaccaga atgtatatta    3420
aggtgtggct ttaggagcag tgggagggta ccagcagaaa ggttagtatc atcagatagc    3480
atcttatacg agtaatatgc ctgctatttg aagtgtaatt gagaaggaaa attttagcgt    3540
gctcactgac ctgcctgtag ccccagtgac agctaggatg tgcattctcc agccatcaag    3600
agactgagtc aagttgttcc ttaagtcaga acagcagact cagctctgac attctgattc    3660
```

```
gaatgacact gttcaggaat cggaatcctg tcgattagac tggacagctt gtggcaagtg    3720
aatttgcctg taacaagcca gattttttaa aatttatatt gtaaatattg tgtgtgtgtg    3780
tgtgtgtgta tatatatata tatgtacagt tatctaagtt aatttaaagt tgtttgtgcc    3840
tttttatttt tgtttttaat gctttgtatt ttcaatgtta gcctcaattt ctgaacacca    3900
taggtagaat gtaaagcttg tctgatcgtt caaagcatga aatggatact tatatggaaa    3960
ttctgctcag atagaatgac agtccgtcaa aacagattgt ttgcaaaggg gaggcatcag    4020
tgtccttggc aggctgattt ctaggtagga aatgtggtag cctcactttt aatgaacaaa    4080
tggcctttat taaaaactga gtgactctat atagctgatc agttttttca cctggaagca    4140
tttgtttcta ctttgatatg actgtttttc ggacagttta tttgttgaga gtgtgaccaa    4200
aagttacatg tttgcacctt tctagttgaa aataaagtgt atattttttc tataaagggc    4260
ttggttattc atttatcctt ctaaacattt ctgagttttc ttgagcataa ataggaagtt    4320
cttattaatc ataagataat tcaccaataa ttttctaaat atctttaatt attctataca    4380
ttaataaatt gattattcca tagaattttt atgtaaacat acttcacact gaatcaagta    4440
tcacagactt gcaggcatac acaccacatt gactatacag ccattttttt tgttatcttc    4500
acagaacttt atagacactt taaattcaat tctctctaga ttacttcagt ctccattaac    4560
cctgttgtat tacacttggt ccttttggca tttgtacctc tctggccgtt ataggttagt    4620
ttccaaccct tcacatcaca aactagtcta tgtgccttgc acgtggaaaa tgtttacatt    4680
ttttaaaaat tttatgctct aggtctgttt ctgaacttca ttaccttact gttaaatctg    4740
aaaattatga aatgaaatcc tcatttaaat ggagctattt cataagtctt gttttgtata    4800
attccgtttt tggttgccat gataaccaat gacaaacaga tggcataaat agaaaaggga    4860
ggatgagcaa atcttccatt cattaacatt aatagaaatt tgttttgaaa gtaattcctc    4920
catttgccca agtctttagc tttatcagac ttcaggatta atgcatccta ccttaccaag    4980
tggtttatac atgagaaaat ggaattgttc aagaagcctc atgtggaaac aatattgtac    5040
ctacccaggt aggttttttac taaagagtga accaaagtga atggtaaaca aaagcaatac    5100
accaaaggca actagaatct tctccacatg aggatagctg aggattctag ggaaaaaaaa    5160
aattgcagac agactaactt ttcccaaggt aattagcaac gttgtagtgc caatgtcatt    5220
tggacagaca aaaatacacc tgaaaataaa gactagctct acaaacaact gtccacacca    5280
caaaccaaag ggaaaacttc ccgtgttcag aatgtgaaaa tttatggtca aaactctggg    5340
ctttaaggat acacccacat ctgtatatag cagtgctgcc aggagcagca ccccacctcc    5400
ccaaataaat gcgcatgtac acatacacat aggcacacac acagagtaca ctgttagttc    5460
acacttcctt tctgtcaatt aattcctaac tgcaaagatg aagggccatg catgataaac    5520
gagactgact actgaattag agcattctgg aaatatagaa gcagcaggaa aagcatagat    5580
ttcacatttt ccaaatacccc acattaaaga aaaaaaaag agtcactaga ttgcaaaaca    5640
aaaatcccac aggcaatgtt tctacaaaaa ttagatggca atgcacactt tcaccccccca    5700 aatatcggag gtagggggtg ccaaatcatc aaccaccgta agatctgcac cgtgtcagca    5760
catgtgtgag aaaagcagag aaacaacaag gtatctgatg cttctgagaa cacgagagct    5820
ctcaaacagc cagcaggtag tcactagata tatagaaggc caggctgaca gcagctgttg    5880
aatctagtag gggtttggcc tagcactcca acaaagctta caagccaggg ctgcctccca    5940
ggagaagatc ctcatactcc tggaagtgga atctaaattg agcaggtcac cagacagatg    6000
``` t                                                                        6001

<210> SEQ ID NO 11
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 11
ccagctgctt ggcgcagacg                                                    20

<210> SEQ ID NO 12
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 12
gccagaaagc tcaaacttga                                                    20

<210> SEQ ID NO 13
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 13
ccacaagctg tccagtctaa                                                    20

<210> SEQ ID NO 14
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 14
ggtcacactc tcaacaaata                                                    20

<210> SEQ ID NO 15
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 15
aaacatgtaa cttttggtca                                                    20

<210> SEQ ID NO 16
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 16
gggaagagtt gttgtgtgag                                                    20

```
<210> SEQ ID NO 17
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 17
agggtggagt cgcactggct                                                      20

<210> SEQ ID NO 18
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 18
acgaaggcga cgcggacggg                                                      20

<210> SEQ ID NO 19
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 19
gccgacggcc ggccggctgc                                                      20

<210> SEQ ID NO 20
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 20
ggtgcacacg ccgatcttgc                                                      20

<210> SEQ ID NO 21
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 21
tctttggcgg tgcacacgcc                                                      20

<210> SEQ ID NO 22
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 22
gcaccatctt tggcggtgca                                                      20
```

```
<210> SEQ ID NO 23
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 23
gcagggagca ccatctttgg                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 24
aagatgcagg gagcaccatc                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 25
ccaccgaaga tgcagggagc                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 26
ccgtaccacc gaagatgcag                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 27
gtacttgcag ctgctctgga                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 28
gggcatgcag cccaccgccc                                              20
```

```
<210> SEQ ID NO 29
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 29
aggcccaacc acggtttggt                                                   20

<210> SEQ ID NO 30
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 30
agggcaggcc caaccacggt                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 31
taagccgcga gggcaggccc                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 32
cccacaggtc ttggaacagg                                                   20

<210> SEQ ID NO 33
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 33
agatgcccat cccacaggtc                                                   20

<210> SEQ ID NO 34
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 34
ccagtctaat gagttaatgt                                                   20

<210> SEQ ID NO 35
```

```
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 35
ttcaagttcc agtctaatga                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 36
ttttccccca gttagaaaaa                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 37
cacaatgttt tgaattgggt                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 38
acatggcaca atgttttgaa                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 39
gtttgacatg gcacaatgtt                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 40
tatttgtttg acatggcaca                                              20

<210> SEQ ID NO 41
<211> LENGTH: 20
```

-continued

```
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 41
tgatagacta tttgtttgac                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 42
gttccactgt caagtcttaa                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 43
tgtactaatg tagttccact                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 44
cattctggtg ctgtgtacta                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 45
taatatacat tctggtgctg                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 46
acaccttaat atacattctg                                              20

<210> SEQ ID NO 47
<211> LENGTH: 20
<212> TYPE: DNA
```

<213> ORGANISM: Artificial Sequence
<220> FEATURE:
<223> OTHER INFORMATION: Antisense directed to human connective tissue
      growth factor (CTGF)

<400> SEQUENCE: 47
taaagccaca ccttaatata                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 48
gtaccctccc actgctccta                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 49
aagatgctat ctgatgatac                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 50
cgtataagat gctatctgat                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 51
aatagcaggc atattactcg                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 52
tacacttcaa atagcaggca                                              20

<210> SEQ ID NO 53
<211> LENGTH: 20
<212> TYPE: DNA
<213> ORGANISM: Artificial Sequence

```
<220> FEATURE:
<223> OTHER INFORMATION: Antisense directed to human connective tissue
      growth factor (CTGF)

<400> SEQUENCE: 53
tcaattacac ttcaaatagc                                                   20

<210> SEQ ID NO 54
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 54
ggagaatgca catcctagct                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 55
atggctggag aatgcacatc                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 56
tcttgatggc tggagaatgc                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 57
gaatcagaat gtcagagctg                                                   20

<210> SEQ ID NO 58
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 58
cattgaaata tcaaagcatt                                                   20

<210> SEQ ID NO 59
<211> LENGTH: 20
<212> TYPE: DNA
<213> ORGANISM: Artificial Sequence
<220> FEATURE:
```

<223> OTHER INFORMATION: Antisense directed to human connective tissue
      growth factor (CTGF)

<400> SEQUENCE: 59
ggctaacatt gaaatatcaa                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 60
aattgaggct aacattgaaa                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 61
gttcagaaat tgaggctaac                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 62
tatggtgttc agaaattgag                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 63
ctacctatgg tgttcagaaa                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 64
tacattctac ctatggtgtt                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 65
gacaagcttt acattctacc                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 66
gatcagacaa gctttacatt                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 67
atgctttgaa cgatcagaca                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 68
atttcatgct ttgaacgatc                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 69
gtatccattt catgctttga                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 70
ccatataagt atccatttca                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

```
<400> SEQUENCE: 71
gaatttccat ataagtatcc                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 72
tctgagcaga atttccatat                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 73
tgtcattcta tctgagcaga                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 74
tttgacggac tgtcattcta                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 75
aacaatctgt tttgacggac                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 76
tgatgcctcc cctttgcaaa                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)
```

```
<400> SEQUENCE: 77
tgccaaggac actgatgcct                                            20

<210> SEQ ID NO 78
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 78
cagcctgcca aggacactga                                            20

<210> SEQ ID NO 79
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 79
gaaatcagcc tgccaaggac                                            20

<210> SEQ ID NO 80
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 80
acctagaaat cagcctgcca                                            20

<210> SEQ ID NO 81
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 81
ttcctaccta gaaatcagcc                                            20

<210> SEQ ID NO 82
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 82
taccacattt cctacctaga                                            20

<210> SEQ ID NO 83
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 83
```
tgaggctacc acatttccta                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 84
taaaagtgag gctaccacat                                            20

<210> SEQ ID NO 85
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 85
caaatgcttc caggtgaaaa                                            20

<210> SEQ ID NO 86
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 86
tagaaacaaa tgcttccagg                                            20

<210> SEQ ID NO 87
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 87
tcatatcaaa gtagaaacaa                                            20

<210> SEQ ID NO 88
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 88
tccgaaaaac agtcatatca                                            20

<210> SEQ ID NO 89
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 89
acccggctgc agagggcgag                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 90
cgcttacccg gctgcagagg                                                    20

<210> SEQ ID NO 91
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 91
gacagggcgg tcagcggcgc                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 92
agtccgagcg gtttctttt                                                     20

<210> SEQ ID NO 93
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 93
aactcagtcc gagcggtttc                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 94
aaagaaactc agtccgagcg                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 95
tggagaaaga aactcagtcc                                                    20

```
<210> SEQ ID NO 96
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 96
gcagctggag aaagaaactc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 97
tggcagcagc tggagaaaga                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 98
agggagcacc atctttggct                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 99
tcacccgcga gggcaggccc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 100
ggaagactcg actcacccgc                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 101
ttagaggaag actcgactca                                              20
```

```
<210> SEQ ID NO 102
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 102
accctgactt agaggaagac                                                    20

<210> SEQ ID NO 103
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 103
tcacgaccct gacttagagg                                                    20

<210> SEQ ID NO 104
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 104
gagaatcacg accctgactt                                                    20

<210> SEQ ID NO 105
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 105
tgggagagaa tcacgaccct                                                    20

<210> SEQ ID NO 106
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 106
ctccctggga gagaatcacg                                                    20

<210> SEQ ID NO 107
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 107
ggtcggcaca gttaggactc                                                    20
```

```
<210> SEQ ID NO 108
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 108
cgttcggtcg gcacagttag                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 109
cctggataag gtatttcccc                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 110
acaaacacca tgtaaaacgc                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 111
gagcacacaa acaccatgta                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 112
tgcgagagca gagcacacaa                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 113
taagctgcga gagcagagca                                              20

<210> SEQ ID NO 114
```

```
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 114
gtcggtaagc tgcgagagca                                            20

<210> SEQ ID NO 115
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 115
ttccagtcgg taagctgcga                                            20

<210> SEQ ID NO 116
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 116
acatgtacct taatgttctc                                            20

<210> SEQ ID NO 117
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 117
gcagaacatg taccttaatg                                            20

<210> SEQ ID NO 118
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 118
taggagcaga acatgtacct                                            20

<210> SEQ ID NO 119
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 119
gttaatagga gcagaacatg                                            20

<210> SEQ ID NO 120
<211> LENGTH: 20
```

```
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 120
tgaaaaatag ttaataggag                                                20

<210> SEQ ID NO 121
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 121
ccactgtttt tcctgtgaaa                                                20

<210> SEQ ID NO 122
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 122
aagttgggtc ctatccactg                                                20

<210> SEQ ID NO 123
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 123
gccctaagtt gggtcctatc                                                20

<210> SEQ ID NO 124
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 124
caagagccct aagttgggtc                                                20

<210> SEQ ID NO 125
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 125
cgtggcaaga gccctaagtt                                                20

<210> SEQ ID NO 126
<211> LENGTH: 20
<212> TYPE: DNA
```

-continued

<213> ORGANISM: Artificial Sequence
<220> FEATURE:
<223> OTHER INFORMATION: Antisense directed to human connective tissue
      growth factor (CTGF)

<400> SEQUENCE: 126
cgggcttata ctaacaagcg                                           20

<210> SEQ ID NO 127
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 127
gataacgggc ttatactaac                                           20

<210> SEQ ID NO 128
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 128
ttggagataa cgggcttata                                           20

<210> SEQ ID NO 129
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 129
tagttttgga gataacgggc                                           20

<210> SEQ ID NO 130
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 130
ttagatagtt ttggagataa                                           20

<210> SEQ ID NO 131
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 131
caatggttag atagttttgg                                           20

<210> SEQ ID NO 132
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 132
cagctcaatg gttagatagt                                                    20

<210> SEQ ID NO 133
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 133
caaaacagct caatggttag                                                    20

<210> SEQ ID NO 134
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 134
tccagcaaaa cagctcaatg                                                    20

<210> SEQ ID NO 135
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 135
ctcattccag caaaacagct                                                    20

<210> SEQ ID NO 136
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 136
aagctctcat tccagcaaaa                                                    20

<210> SEQ ID NO 137
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 137
tacacaagct ctcattccag                                                    20

<210> SEQ ID NO 138
<211> LENGTH: 20
<212> TYPE: DNA
<213> ORGANISM: Artificial Sequence
<220> FEATURE:

<210> SEQ ID NO 138
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 138
ggttgctatt acacaagctc                                          20

<210> SEQ ID NO 139
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 139
ctggtggttg ctattacaca                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 140
gaaaactggt ggttgctatt                                          20

<210> SEQ ID NO 141
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 141
tagtggaaaa ctggtggttg                                          20

<210> SEQ ID NO 142
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 142
ttaactaacc ctgtggaaga                                          20

<210> SEQ ID NO 143
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 143
tgtcttgaat taactaaccc                                          20

<210> SEQ ID NO 144
<211> LENGTH: 20
<212> TYPE: DNA
<213> ORGANISM: Artificial Sequence
<220> FEATURE:
<223> OTHER INFORMATION: Antisense directed to human connective tissue growth factor (CTGF)

<400> SEQUENCE: 144
tggaatgtct tgaattaact                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 145
gccagagcct ctcttggaat                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 146
aaaaatagcc agagcctctc                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 147
tgtccaaaaa tagccagagc                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 148
tgctatgtcc aaaaatagcc                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 149
tcatttgcta tgtccaaaaa                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

-continued

<400> SEQUENCE: 150
gagtctcatt tgctatgtcc                                               20

<210> SEQ ID NO 151
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 151
agtttgagtc tcatttgcta                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 152
gaggaagttt gagtctcatt                                               20

<210> SEQ ID NO 153
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 153
cttctgttgt ctgacttctg                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 154
cctctgtgtt ttagtcttct                                               20

<210> SEQ ID NO 155
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 155
tttcttcaac cctctgtgtt                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 156
ggagtggctt tcttcaaccc                                                    20

<210> SEQ ID NO 157
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 157
aggaagacaa gggaaaagag                                                    20

<210> SEQ ID NO 158
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 158
ttctaaggaa gacaagggaa                                                    20

<210> SEQ ID NO 159
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 159
tgcccttcta aggaagacaa                                                    20

<210> SEQ ID NO 160
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 160
ggatgcgagt tgggatctgg                                                    20

<210> SEQ ID NO 161
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 161
ccagctgctt ggcgcagacg                                                    20

<210> SEQ ID NO 162
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 162
gccagaaagc tcaaacttga                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 163
ccacaagctg tccagtctaa                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 164
ggtcacactc tcaacaaata                                          20

<210> SEQ ID NO 165
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 165
aaacatgtaa cttttggtca                                          20

<210> SEQ ID NO 166
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 166
tgacatggca caatgttttg                                          20

<210> SEQ ID NO 167
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 167
ccttccctga aggttcctcc                                          20